United States Patent
Miller et al.

(10) Patent No.: US 10,190,945 B2
(45) Date of Patent: Jan. 29, 2019

(54) PARTICULATE MATTER/NUMBER SYNCHRONIZATION MEASUREMENT DEVICE

(71) Applicant: 3DATX Corporation, Buffalo, NY (US)

(72) Inventors: David W. Miller, Clarence Center, NY (US); John William Hynd, Clarence Center, NY (US); Gurdas S. Sandhu, Cary, NC (US); Andrew D. Burnette, El Dorado Hills, CA (US); Karl Ropkins, Ilkley (GB)

(73) Assignee: 3DATX Corporation, Buffalo, NY (US)

( * ) Notice: Subject to any disclaimer, the term of this patent is extended or adjusted under 35 U.S.C. 154(b) by 70 days.

(21) Appl. No.: 15/512,266

(22) PCT Filed: Sep. 18, 2015

(86) PCT No.: PCT/US2015/050950
§ 371 (c)(1),
(2) Date: Mar. 17, 2017

(87) PCT Pub. No.: WO2016/044730
PCT Pub. Date: Mar. 24, 2016

(65) Prior Publication Data
US 2017/0248494 A1 Aug. 31, 2017

Related U.S. Application Data

(60) Provisional application No. 62/052,525, filed on Sep. 19, 2014.

(51) Int. Cl.
*G01M 15/10* (2006.01)
*G01N 15/02* (2006.01)
(Continued)

(52) U.S. Cl.
CPC .......... *G01M 15/102* (2013.01); *G01N 15/00* (2013.01); *G01N 15/02* (2013.01); *G01N 15/0656* (2013.01); *G01N 2015/0046* (2013.01)

(58) Field of Classification Search
USPC ....................................... 73/114.71
See application file for complete search history.

(56) References Cited

U.S. PATENT DOCUMENTS 5,895,869 A * 4/1999 Von Behrens ..... G01N 15/1404
73/865.5
6,308,130 B1 10/2001 Vojtisek-Lom
(Continued)

FOREIGN PATENT DOCUMENTS

EP 1972925 A1 9/2008
WO 0179804 A1 10/2001

*Primary Examiner* — Eric S McCall
(74) *Attorney, Agent, or Firm* — Hodgson Russ LLP

(57) ABSTRACT

An emissions measurement system capable of providing an accurate, real-time estimate of particle number (PN)/particulate matter (PM) within exhaust is disclosed. The system is capable of accurately differentiating the size and composition of PM/PN by synchronizing dissimilarly configured sensors. The exhaust may be generated by an internal combustion engine, in which case the system may be sequentially connected to the exhaust from the internal combustion engine.

21 Claims, 15 Drawing Sheets

(51) Int. Cl.
*G01N 15/06* (2006.01)
*G01N 15/00* (2006.01)

(56) References Cited

U.S. PATENT DOCUMENTS

| | | | | |
|---|---|---|---|---|
| 6,435,019 | B1* | 8/2002 | Vojtisek-Lom | G01M 15/108 |
| | | | | 73/114.31 |
| 6,965,240 | B1* | 11/2005 | Litton | G01N 15/0656 |
| | | | | 324/448 |
| 8,915,119 | B2* | 12/2014 | Ueno | F01N 9/002 |
| | | | | 73/23.33 |
| 9,605,578 | B1* | 3/2017 | Qi | F01N 9/002 |
| 2009/0229250 | A1* | 9/2009 | Yamakage | G01N 15/0205 |
| | | | | 60/276 |
| 2010/0206042 | A1 | 8/2010 | Johns et al. | |
| 2011/0072789 | A1* | 3/2011 | Konstandopoulos | F01N 3/021 |
| | | | | 60/276 |
| 2011/0285410 | A1* | 11/2011 | Aoki | G01N 15/0656 |
| | | | | 324/686 |
| 2012/0186330 | A1* | 7/2012 | Ueno | F01N 9/002 |
| | | | | 73/23.33 |
| 2012/0239308 | A1 | 9/2012 | Miller et al. | |

* cited by examiner

PARTICULATE MATTER/NUMBER SYNCHRONIZATION MEASUREMENT DEVICE

CROSS-REFERENCE TO RELATED APPLICATIONS

This application claims priority to the provisional patent application entitled "Particulate Matter/Number Synchronization Measurement Device," filed Sep. 19, 2014 and assigned U.S. App. No. 62/052,525, the disclosure of which is hereby incorporated by reference.

FIELD OF THE DISCLOSURE

The present disclosure relates generally to an improved particulate matter ("PM," or the total mass of the particulate contained in a sample) and/or particle number ("PN," or the total number of particles that comprise the particulate contained in a sample) measurement device.

BACKGROUND OF THE DISCLOSURE

Vehicle and transportation sector-related emissions continue to be a leading source of greenhouse gas (GHG) and air pollution in urban areas around the globe. As an example, there were over 260 million vehicles in the United States (U.S.) in 2012 that emitted 33% (1,750 million metric tons) of total U.S. carbon dioxide ($CO_2$) emissions. In the same year, the U.S. transportation sector share of total U.S. emissions for carbon monoxide (CO), nitrogen oxides ($NO_x$) and PM were 54%, 59%, and 8%, respectively. Therefore, significant resources continue to be focused on emission reduction tactics which typically fall into two categories: current fleet inventory upgrade (e.g., roadside and/or engine bay inspection and maintenance (I/M) programs, aftermarket engine/vehicle/fuel programs, etc.) and new vehicle manufacturing (e.g., revisions of emissions control standards for newly manufactured vehicles, etc.).

The U.S. Environmental Protection Agency (USEPA) defines airborne particulate as "a complex mixture of extremely small particles and liquid droplets . . . made up of a number of components, including acids (such as nitrates and sulfates), organic chemicals, metals, and soil or dust particles." In recent decades, the USEPA, like many other environmental regulatory agencies, has invested significant time, effort, and resources in a wide range of particulate monitoring activities. Early vehicle exhaust particulate monitoring programs employed relatively crude gravimetric methods such as capturing particulate emissions samples on pre-cleaned and weighed filter papers and re-weighing these post-sampling to determine PM mass by difference.

Despite the highly labor-intensive nature of these methods, refinements of these early gravimetric methods (typically employing more inert filter substrates) are still widely used even today. However, significant time and effort has also been focused on the development of other particulate monitoring techniques, most notably methods that could be automated to increase quantitative accuracy, increase sampling efficiency, reduce sampling errors, and reduce associated costs. In more recent years these automated methods have become the basis of more recent rounds of environmental particulate regulation.

The earliest automated particulate measurement technologies were based on measurement principles that provided mass measures or measures that could be readily calibrated against mass measures. Two examples are tapered element oscillation microbalance (TEOM) methods used for routine automatic monitoring of adherence to ambient PM air quality standards and opacity-based methods used in vehicle exhaust PM emissions TIM inspection testing procedures.

This early focus on PM may have reflected both a design to align these newer methods with more established gravimetric testing procedures and an acknowledgement that these measurement technologies were likely the most convenient and accurate options at the time. However, as particulate sources became cleaner in response to PM-focused regulations and associated consumer demand, investigators observed that emission source particulate size distributions tended to become finer and that the number of ultra-fine particles in ambient air is more closely correlated with health effects than the total mass of those particles.

More recently, the development of a PN measurement system by the European Union in 2007 was to enable a more accurate and repeatable identification process of particulates (individual emitted particles). Additional EU objectives were to minimize required changes to the current type approval facilities such as laboratories, to employ an understandable metric, and for the system to be simple to operate. The EU PN system was developed to avoid the possible requirement for correction factors, an issue that has hampered the development of similar measurement initiatives in the U.S.

Accurate emission(s) data are required for a wide range of vehicle and point-source related applications in order to properly evaluate the impact of emission reduction strategies. However, given the complex and (perhaps more importantly) evolving nature of particulate emissions, a single PM or PN metric is unlikely to provide a robust "catch-all" metric for emission-reduction activities. Therefore, it is important to differentiate between the differing sizes of PM/PN in order to both better understand the process that produced them and aid in the identification of potential solution(s) for their reduction. Atmospheric particulate sizes typically range from a few nanometers to tens of micrometers in diameter. The coarsest material (typically 10 micrometers and larger) is predominantly from biological sources (e.g., spores, pollen, bacteria, etc.) and/or mineral sources (e.g., land erosion, construction work, etc.). Finer particles (less than a micrometer) are typically formed by nucleation, condensation, and agglomeration processes, such as a result of atmospheric chemistry and combustion processes.

PM/PN that originates from combustion processes are typically of interest.

Particles smaller than 0.1 micrometer ("ultra-fines") formed as the result of fuel combustion/exhaust emissions processes are associated primarily with internal combustion engines, such as those in on-road, off-road, and non-road vehicle activities. Such particulates have been cited as dangerous due to toxic trace compounds (e.g., heavy metals, polycyclic aromatic hydrocarbons, etc.) often contained in the particulates. The USEPA and the European Union's Joint Research Centre (JRC) have both declared that the concentration of such particles is highly variable, and appears to demonstrate a significant pattern of variation, especially close to urban areas and traffic congestion.

Traditionally, vehicle testing is often performed in a laboratory with a chassis or engine dynamometer, following government-approved testing cycles (e.g., Euro IV, U.S. FTP, or other global standards). However, these standard test procedures, much like the traditional gravimetric PM measurement procedures, are no longer representative of their real-world counterparts and the growing gap between the emission reductions and fuel savings routinely achieved by modern cars on these test cycles and their on-road (or "off cycle") performance has been widely reported.

Investigators already widely acknowledge the "off-cycle" gap to be of the order of 40-60% for fuel consumption and $CO_2$ emissions, and up to 400% (4 times approval levels) for $NO_x$ emissions. Although the challenges associated with real world measurement of vehicle PM/PN emissions using current technology significantly hinder the direct measurement of similar trends for particulates, indirect measurement methods, most notably tunnel studies, indicate that these also may be orders of magnitude higher than lab-based measurements.

Concerns about these "off-cycle" emissions have led to an increased demand for real-world vehicle emission data and for new regulations based on real-world vehicle performance.

Portable Emissions Measurement Systems (PEMS) are vehicle monitoring platforms that can be temporarily attached to a target vehicle to provide a direct measure of vehicle emissions as the vehicle is used in actual service. For example, the "Real-time On-road Vehicle Emissions Reporter" (ROVER) disclosed by the USEPA is an on-board testing system temporarily mounted on a vehicle for the purposes of measuring real-world emissions while the vehicle is driven on the roadway. Commercial systems, many based on the original ROVER concept, are now used to collect real-world vehicle emission data.

However, the disadvantages of the conventional PEMS approach are also significant. Due to the fact that all commercially available PEMS equipment requires that the sample be transported well away from the exhaust stack or tailpipe, issues such as heat changes, sample degradation, power requirements, and system complexity typically introduce accuracy and dependability problems. These issues significantly impact the investigation of emission reduction tactics, as PEMS are limited by their design, size, and weight, and thereby limit the amount of real-world vehicles and test data that can be collected in a "true" real-world scenario. Simply put, PEMS-related activities (equipment installation, maintenance, upkeep, charging, filter replacements, supervised operation, uninstall, etc.) often hinder the ability to collect truly representative "real-world" data in sufficient volumes and/or at reasonable costs.

Present vehicle exhaust PM/PN PEMS have significant power demands attributable to the sensor design, sample dilution, and flow measurement(s). Due to these challenges, currently-available PEMS do not have the capability to run self-powered for more than a few hours or, in some cases, even more than a few minutes, which significantly restricts sampling options. Also, the accompanying weight of such systems demands that the device(s) be mounted well away from the exhaust outlet, further limiting the target vehicle's performance under typical driving conditions. In addition, the associated use of long sample line(s) required to transport the sample to the sensors introduces a range of sample integrity issues that particulates are particularly sensitive to.

One problem is that increased power to heat or condition the sample while it is being transferred from the exhaust to the sensor adds significantly to the power requirements and weight of the PEMS unit. Additionally, the increased length of the sample line(s) increases the surface area for interaction with the sample (e.g., water vapor condensation and particulate deposition), which, in turn, must be accounted for and expelled/corrected.

There are several problems with increased length of sample tubes and/or lines that PM/PN measurements are particularly sensitive to.

First, the additional length means an increase in the power required to pump a sample at a given flow rate due to flow friction, which increases with the length of the sample tubing, and necessitates a more powerful pump and a need for a larger, more powerful battery.

Second, in addition to the direct increase to the size and weight of the testing device, longer sample lines introduce additional weight, bulk, and complexity to the testing process. They must be properly and safely clamped, secured, or tied along the entire run of sample line. This increases the chance of safety issues, such as improperly secured lines that get caught up in running machinery and moving parts, etc. Length negatively affects the reliability of the system. The increased length of the sample line(s) also increases the surface area for particulate deposition, which, in turn, must be accounted for and corrected.

Third, a longer length of sample tubing requires a proportionally increased amount of insulation and/or supplied heat to prevent the condensation of liquid water and deterioration of the sample as it travels to the testing device and cools. Most exhaust gas samples contain significant amounts of water. If this is allowed to condense during sample transfer or analysis, the resulting liquid water can interact with and degrade some pollutants, most notably the more reactive gaseous species and particulates. However, the increased insulation adds significant weight and bulk to the sample lines, and in many cases PEMS units require additional dedicated power supplies for the sample line(s) heaters.

Fourth, as sample line length increases, it also increases the amount of setup/teardown time required to perform testing. The additional time required to properly install long sample lines directly impacts the number of accurate and safe tests that can be completed in a shift.

Finally, another problem with present vehicle PM/PN PEMS is their focus on a single sensing method. Although these current PM/PN systems have been accepted as accurate by various federal, state, local, and global evaluation standards, a single measurement method-based solution is typically advocated by regulatory agencies. Extremely accurate sensing of one variable may require equipment of large size and weight. It also means that associated reliability of any analyte measurement is intrinsically linked to one measurement principle and, therefore, requires the continued representativeness of the associated metric.

Each sensing technique uses a different approach and has a different bias with the PM/PN that is being sensed and recorded. Unlike gaseous pollutants, such as $CO_2$ or $NO_x$, PM/PN is not one chemical species. The exact constitution of PM/PN emissions includes complex structures, for example a solid phase carbon particle with liquid phase hydrocarbons adsorbed onto its surface, and both of these phases can incorporate, adsorb, or absorb numerous species in numerous distributions. Furthermore, PM/PN exists in a wide range of sizes, and health concerns have been associated with PM/PN of aerodynamic diameter from 10 micrometers to less than 100 nanometers. Any one measurement technique will provide results that are biased by the type of PM/PN the measurement technique is most sensitive to and no one measurement technique can be sensitive to the complete range of PM/PN chemical and physical structures. Thus, PM/PN, by its very nature, cannot be fully characterized by any one sensing technique, however accurate it may be.

This point is illustrated by considering the existing California Heavy-Duty I/M test procedure. This incorporates a measurement based on opacity (a measure of light extinction). When this was first introduced, it was a highly effective test because it provided a good measure of the larger coarser material that then represented a significant fraction of exhaust PM mass. More recent improvements to vehicle engine management systems and exhaust emissions abatement systems have both reduced the amount of particulate emitted by vehicles and the size ranges it is typically emitted in. The opacity method is not sensitive to the smaller amounts of finer material that modern vehicle typically produce. As a result, a faulty modern vehicle can emit large amounts of particulates, often well above regulatory limits, but still pass an TIM test because the emitted particulate is too fine to be detected using opacity.

What is needed is an improved PM and PN measurement device that is both easier to deploy (e.g., smaller, lighter weight, lower energy demand) and provides an ability to provide both a measure of PM/PN on the basis of current standards and also identify, characterize, or map onto the changing properties of particulates as their emission sources change.

BRIEF SUMMARY OF THE DISCLOSURE

In a first embodiment, an emissions measurement system is provided. The emissions measurement system includes an emissions sample inlet, at least three sensors connected to the emissions sample inlet, and an emissions sample outlet connected to the at least three sensors. The sensors are sequentially connected in a linear arrangement. Each of the at least three sensors is configured to perform a different measurement of a sample.

Each of the sensors may be selected from the group consisting of, for example, a laser light opacity sensor, a light scattering sensor, a particle ionization sensor, a particle acoustic measurement sensor, and an electrostatic precipitation sensor. In an instance, the sensors include a laser light opacity sensor, a light scattering sensor, and a particle ionization sensor. One of the sensors may be a laser light opacity sensor configured to use a blue laser.

The sensors may be configured to be synchronized. A processing unit may be wirelessly connected to the sensors. The processing unit may be configured to provide results based on data provided by the sensors. The processing unit may be configured to triangulate the data provided by the sensors.

In a second embodiment, a method of measuring emissions is provided. The method includes linearly transporting an emissions sample through at least three sensors and calculating either a particle number (PN) or particulate matter (PM) measurement for the emissions sample using data from the sensors. Each of the sensors is configured to perform a different measurement of the emissions sample.

The method may further include triangulating the data from the at least three sensors. The calculating may use a proportionality factor, a weighted linear integral factor, or a non-linear integral factor. Each of the sensors may be selected from the group consisting of, for example, a laser light opacity sensor, a light scattering sensor, a particle ionization sensor, a particle acoustic measurement sensor, and an electrostatic precipitation sensor.

In a third embodiment, a method of generating a particulate matter (PM) or particle number (PN) is provided. The method includes receiving readings of an exhaust sample from at least three different sensors, applying a union function to the readings, applying an intersect function to the readings, and identifying a quantity of a pollutant within the exhaust sample. The exhaust sample is linearly transported through the sensors. Each of the readings includes at least one of a PM and a PN. The quantity may include a mass of particles, a number of particles, or a concentration of particles. The identifying may be based on at least one parameter associated with another exhaust sample. The method may include filtering the readings from the sensors prior to applying the union function or the intersect function. The method may include triangulation of the readings.

In a fourth embodiment, an emissions measurement system is provided. The emissions measurement system includes a sensor cartridge defining an emissions sample inlet and an emissions sample outlet, at least three sensors disposed within the sensor cartridge between the emissions sample inlet and emissions sample outlet, a sample probe that is fluidically connected to the emissions sample inlet, and a battery disposed in the sensor cartridge that is configured to provide power to the sensors. The sensors are sequentially connected in a linear arrangement. Each of the sensors is configured to perform a different measurement of a sample.

Each of the sensors may be selected from the group consisting of, for example, a laser light opacity sensor, a light scattering sensor, a particle ionization sensor, a particle acoustic measurement sensor, and an electrostatic precipitation sensor. In an instance, the sensors include a laser light opacity sensor, a light scattering sensor, and a particle ionization sensor. One of the sensors may be a laser light opacity sensor configured to use a blue laser.

The sensors may be configured to be synchronized. A processing unit may be wirelessly connected to the sensors. The processing unit may be configured to provide results based on data provided by the sensors. The processing unit may be configured to triangulate the data provided by the sensors.

A temperature in any of the sensors may be equal thereby reducing water vapor and condensation buildup.

The sensor cartridge may include shock absorbing materials disposed in the sensor cartridge. The sensor cartridge may be configured to be connected to an exhaust of an internal combustion engine.

In a fifth embodiment, a method of measuring emissions is provided. The method includes directing an emissions sample into a sensor cartridge, linearly transporting the emissions sample through at least three sensors, directing the emissions sample out of the sensor cartridge, transmitting data from the sensors to a processing unit, and calculating either a particle number (PN) or particulate matter (PM) measurement for the emissions sample using data from the sensors. Each of the sensors is configured to perform a different measurement of the emissions sample.

The method may further include triangulating the data from the at least three sensors using the processing unit. The calculating may use a proportionality factor, a weighted linear integral factor, or a non-linear integral factor. Each of the sensors may be selected from the group consisting of, for example, a laser light opacity sensor, a light scattering sensor, a particle ionization sensor, a particle acoustic measurement sensor, and an electrostatic precipitation sensor.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Figure 1:
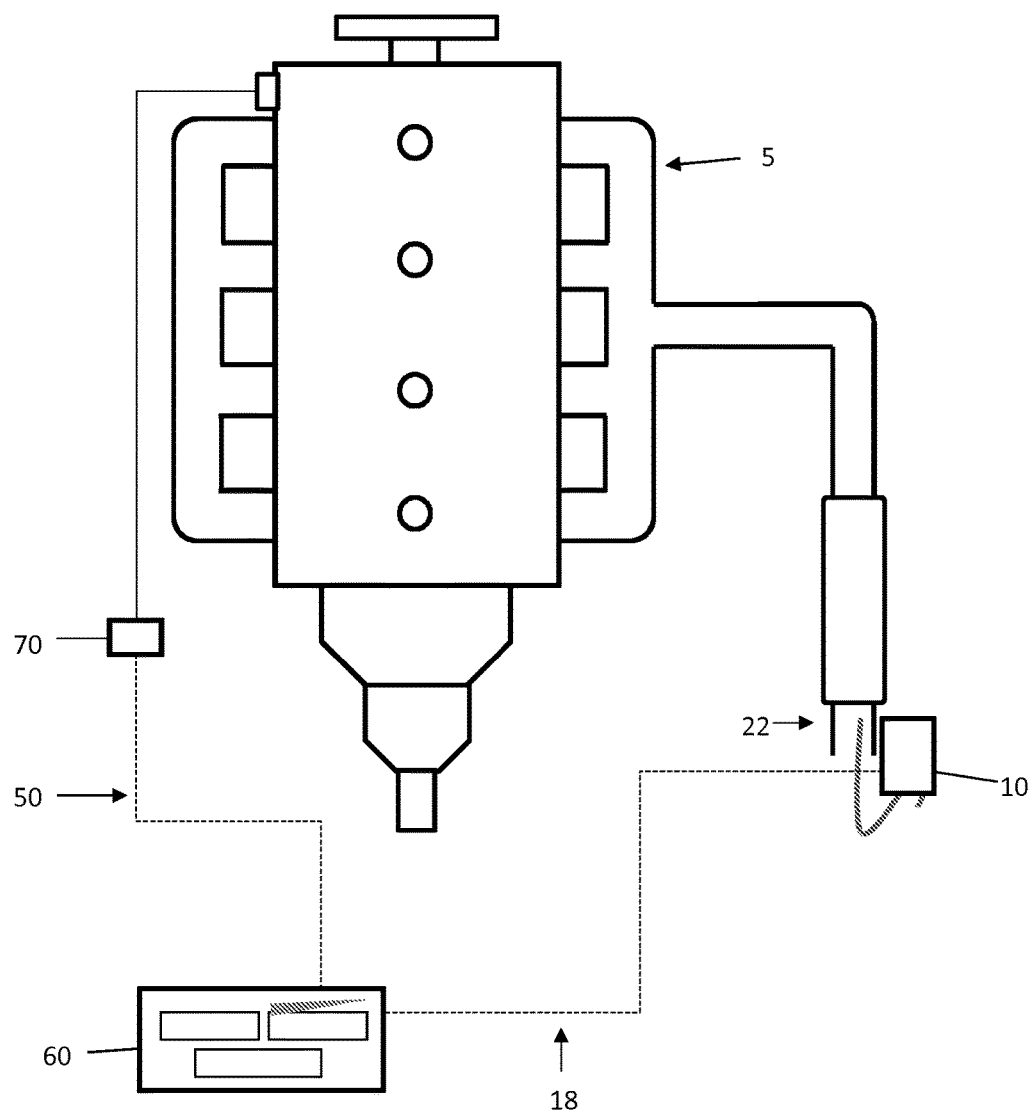
FIG. 1 is a schematic of a first embodiment of the improved PM/PN emissions measurement system mounted to an exhaust stack or tailpipe in accordance with the present disclosure.

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

The embodiments of the measurement device disclosed herein use three or more "triangulated" complementing and sufficiently accurate PM/PN sensing techniques in a compact and lightweight design, supplemented with software algorithms, to capture the nuances of vehicle exhaust PM/PN otherwise missed by traditional PEMS-based PM/PN measurement systems. The triangulation technique (collecting three or more separate measures of different particulate properties and integrating these to provide a multidimensional description of the sampled particulate) can provide a number of advantages over conventional single metric PM/PN measurement-based systems because it creates a superior, more robust basis for measurement. Further, the underlying logic behind the triangulation approach is the premise that no single method will ever adequately describe a complex and variable analyte like PM/PN, and that multiple complementary measures of the same sample mapping their similarities and dissimilarities provide a superior description of the PM/PN. Further, the principle can be extended to calibration to provide surrogate measures for instrumental techniques less readily deployed as part of mobile PEMS measurement work. Mapping three or more sensor responses onto the response profile of a conventional measurement method provides a mechanism for the generation of "reference measurement like" data, which are typically superior to a conventional direct reference method calibration, even using the most similar of the sensor set.

The availability of three or more data sets also allows for routine fault testing. While each sensor will respond differently to particulate, they will each exhibit behaviors that can be mapped onto behavior for two or more other sensors. As a sensor begins to fail or after a sensor is damaged, its response characteristics will no longer map onto other sensor behavior in the same fashion, indicating a problem. Perhaps the easiest way to envision this is to consider a three-sensor array comprising opacity, light scattering, and ionization sensors. The opacity sensor would be more responsive to coarser material, the ionization sensor would be more responsive to finer material, and the light scattering sensor response would sit somewhere between the other two. The light scattering sensor response could be mapped onto the other two sensors' responses, both individually and in combination. While the associated relationships would be not absolute, these and associated degrees of agreement could also be determined along with baseline and noise characteristics, and used to benchmark sensor performance and provide an early indication of atypical behavior, itself a potential indicator of sensor failure or sampling issues. Thus, three or more data sets may allow determination that a sensor is faulty or provide sufficiently accurate results even if a sensor is damaged or failing.

Disclosed herein is a small, lightweight, sample-parcel synchronized multi-chamber device to measure PM and PN concentration from internal combustion engines (ICE) and other sources of particulate. The sensor design has the ability to obtain second-by-second PM/PN concentration from the ICE in, for example, either a dedicated "pass/fail" lane-testing configuration or as a field unit. The device can be used in, for example, roadside vehicle stop-and-spot-check testing procedures (so-called "snap-acceleration testing"), conventional engine or chassis dynamometer testing with or without sample dilution, and PEMS style in-vehicle mobile emission measurement work. The embodiments disclosed herein provide several unique, complementing, and simultaneous measurements of the sample parcel as it passes through a common sensor cartridge for a more accurate and multi-dimensional observation of the sample parcel. The sample may be air, exhaust gas and/or condensate sample. The embodiments disclosed herein also reduce the physical footprint of the device (relative to existing systems) to allow the device to be easily attached to the frame, exhaust, or stack of the vehicle in order to: reduce as much distance as possible between the exhaust outlet and the device inlet to reduce sample degradation, heat loss, and water condensation; reduce weight so as to safely transport and attach the device without damaging the frame, exhaust, or stack of the vehicle; and/or rapidly attach, remove, and redeploy the device between vehicles in order to increase the throughput of individual tests and/or test vehicles. The embodiments disclosed herein also reduce the amount of power consumption typically required of existing sample systems by removing the power demand associated with resistance heat for conditioning sample lines and housing chambers.

The embodiments disclosed herein also increase device operating time compared to conventional PEMS PM/PN measurement systems because this lower energy demand system can be operated on battery power for longer periods of time. Furthermore, the potential to run the device for several hours on internal battery power means the device can be used in situations where external power supplies, for example access from the vehicle's own electrical system or a dedicated on-board generator or external battery unit, are not feasible.

The embodiments disclosed herein also consolidate the multiple sample sensors into a common, rapidly replaceable cartridge in order to reduce/eliminate downtime typically associated with existing measurement systems. The embodiments disclosed herein also can wirelessly transmit second-by-second data from the sensors directly to a computer, tablet, smart phone, or other device in order to provide data/information regarding the measured variables and measuring equipment status in real-time while further reducing installation time required for hard-wired communications.

As used herein, "exhaust" can refer to matter expelled from a tailpipe or stack and "emissions" can refer to the specific pollutants in the exhaust. Emissions may be further differentiated using terms such as "exhaust emissions" or "tailpipe emissions" to distinguish between exhaust emissions, evaporative emissions, or crankcase emissions. However, the term emissions generally refers to any type of exhaust.

The real-world operating conditions of an ICE are constantly changing due to constantly-changing engine power demand, which in turn means the exhaust constituents change from one instant to another. For example, instantaneous driver behavior (e.g., how hard the driver presses down on the accelerator or when the driver typically changes gears) influences a wide range of factors, including the instantaneous engine revolutions per minute (RPM), intake manifold absolute pressure (MAP), and air-to-fuel ratio (AFR). In addition, there are many other design and operating parameters, which do not change instantaneously, but that can also affect the exhaust gas character. Some examples are engine size, engine tuning, fuel type, vehicle maintenance condition, post-combustion emissions controls, and ambient conditions. As a result, PM/PN characteristics (e.g., size distribution, elemental carbon content, average composition of adsorbed pollutants, etc.) are complex and highly dynamic. Traditional PM/PN instrument design trends have favored the step-wise modification of existing laboratory instrumentation for use in PEMS-style application, and the continuous improvement on a single, specific (selected) sensor technique as a mechanism to increase single metric measurement accuracy. Unfortunately, the associated instrument and sensor solutions are typically much larger and arguably more over-engineered than purpose-built counterparts. The financial logic behind this trend is straightforward: it is easier and more cost effective for a manufacturer to do minimal work to retrofit an existing laboratory instrument for on-road testing than it is to build dedicated device. The trade-off, however, for such conservative manufacturing strategies is that the "state-of-the-art" systems tend to be large, cumbersome devices with relatively large power demands which are often poorly suited to their application. As mentioned above, a sensory array measurement strategy based on several differing sensing techniques is a highly-informative technique.

It was not expected that a dissimilar set of smaller and less accurate sensors could provide an adequate PM/PN description. However, in addition to a reduced power demand and a smaller footprint device that is more readily deployed in a much wider range of emission measurement applications, the combination of several simplified "non-state-of-the-art" low-tech, less-accurate sensor devices into an array would, while arguably providing a less accurate direct measure of any one PM/PN metric, provide a multidimensional PM/PN description which when considered in combination can provide a more comprehensive record of PM/PN emissions. Therefore, the use of less accurate sensors can provide not only a measurement of the amount of particulate emitted from a vehicle, but also a set of diagnostics that may help to identify the nature of the emissions, or even the specific engine or exhaust system issue that led to that emission increase.

So, rather than a very accurate measure of one metric, which is by the nature of PM/PN unlikely to be the single most informative option of all situations, embodiments of the device disclosed herein are intended to provide several less accurate but complementary and arguably much more all-encompassing measures of any given PM/PN sample.

Additionally, a feature of this device is that these sensors can measure the same sample parcel in series rather than simultaneously sampling from the same exhaust and measuring in parallel. Thus, the sensors are fluidically connected in series. As the same sample is "seen" by each sensor in turn, the separate sensor data time-series can be aligned and integrated to provide more information in real-time (or near-real-time) than less well aligned sampling configurations (e.g., separate sensors deployed in configurations where offsets were unknown or parallel configurations in which the sensors sampled from slightly different exhaust sampling points).

Also, an embodiment of the device disclosed herein can make use of laser light which is farther from the infrared wavelength (e.g., spectral peak of 550-570 nm) than lasers typically used in competing measurement systems (e.g., spectral peak of 660 nm) to increase the inherent signal to noise ratio of the system, thereby increasing its sensitivity relative to other opacity and scattering systems if they were simply reduced to a size similar to these components.

In short, it would not be assumed that multiple less accurate sensors could provide a more accurate measurement of any single metric, the traditional goal of many previous instrument development programs and the USEPA (PM) and the EU (PN) regulatory strategies. However, an approach based on the integration of multiple reasonably accurate measurements of complementary metrics can provide robust measure of multiple metrics, a more comprehensive description of PM/PN, and thereby an ability to incorporate measures that will be sensitive to the changing nature of PM/PN emissions In effect, these various sensor advantages and strengths may not only cancel out the weaknesses of the other sensors, but actually reinforce each other and provide a superior view of the actual instantaneous character of PM/PN emissions in real-time. Therefore, simultaneously capturing different characteristics of particulate matter using different sensing techniques of the exhaust sample provides a unique, individual signature of the constantly varying "collective" characteristic of the particulate matter emissions sample. The system is capable of accurately differentiating the size, striation (e.g., "category" of pollutant), and composition (e.g., make up of pollutant) of PM/PN by synchronizing dissimilarly configured sensors.

Recent analysis of multiple sensors attuned to measuring the same sample parcel has indicated that the simultaneous multi-dimensional measurement provides a more accurate, triangulated image of the PM/PN specifics such as, for example, particle distribution, size, coarse/fine attributes, and potentially even mass. This is illustrated in FIGS. 13A-13D.

Figure 13A:
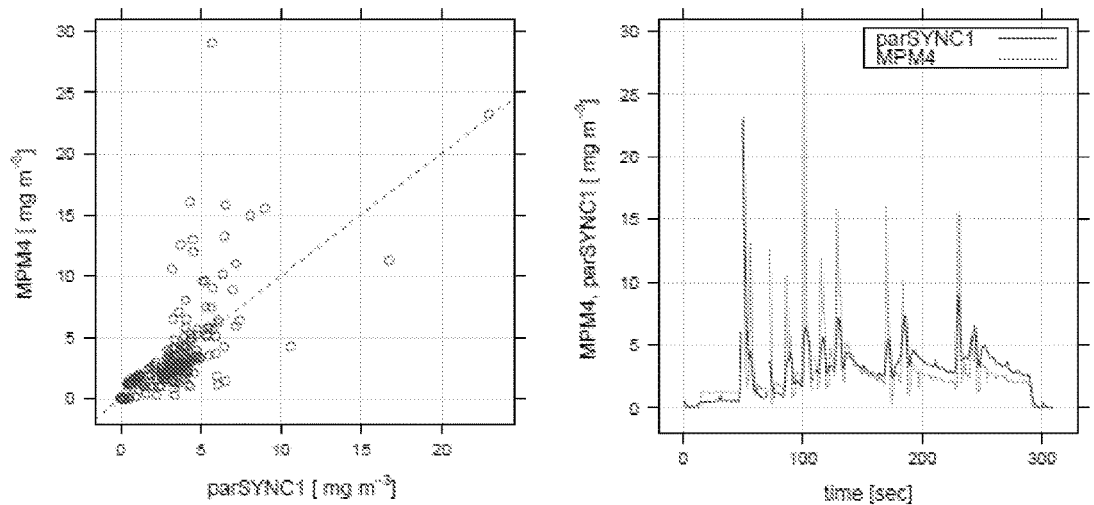
FIG. 13A-13D illustrate analysis of data from sensors in accordance with the present disclosure.
Figure 13B:
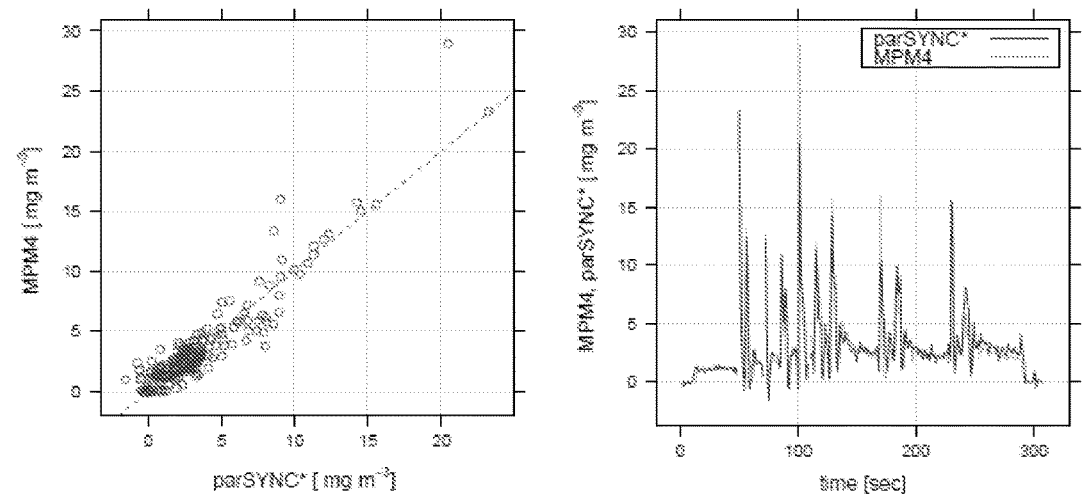

In FIG. 13A and FIG. 13B, an embodiment of the device disclosed herein using a single scattering sensor (labeled "parSYNC1") is compared to a reference method (MAHA MPM4 PM Analyzer). In the example used, the degree of agreement was 75% (Pearson correlation coefficient, R, 0.75). During the same work, similar and less strong agreement were observed for the opacity and ionization sensors, respectively, namely 75% and 42%. If any of these measurement data series were used individually, they would only provide an approximate indication of the reference method output. Predictive power is improved if the sensor outputs are used in combination.

Figure 13C:
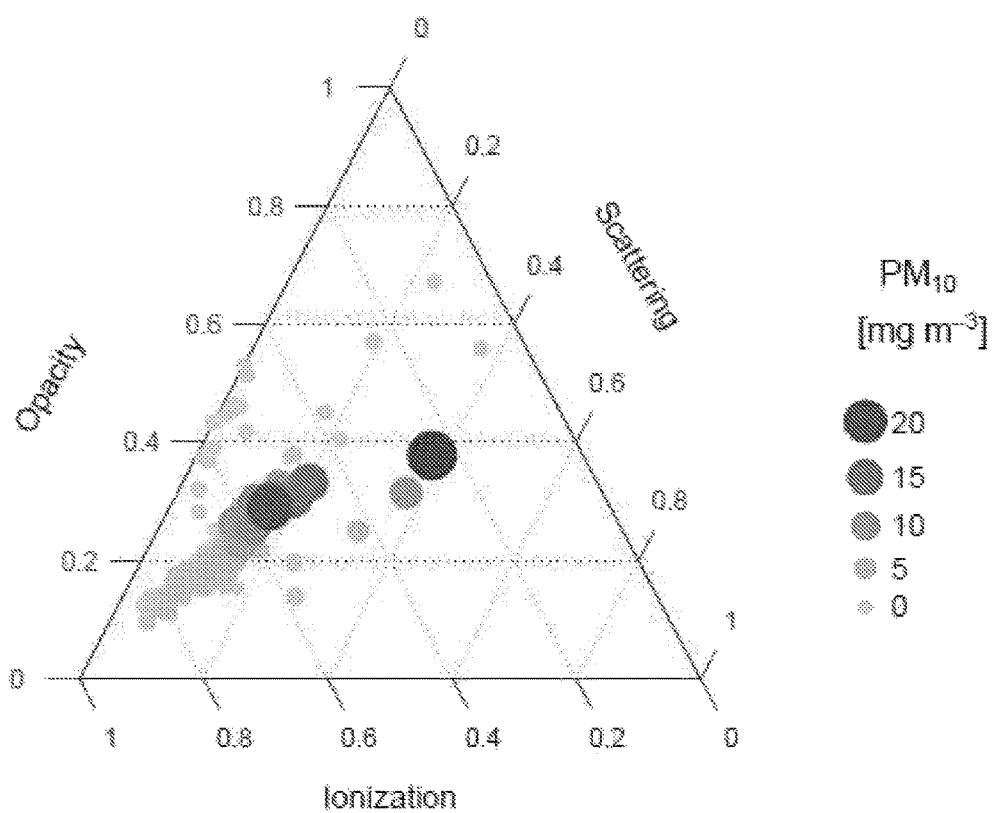

A triangle plot of the relative responses of three sensors (opacity, scattering and ionization) to particulates in vehicle exhaust gas sampled as the vehicle's engine is seen in FIG. 13C. FIG. 13C illustrates the multidimensional nature of the sample. The individual sensors respond to subtly different characteristics of the particulate.

Consistent with this observation, an integrated two sensor (opacity and light scattering) solution, denoted by the term parSYNC*, provided improved agreement with the same reference method, namely 92% (FIG. 13B, Pearson correlation coefficient, R, 0.92) compared with the 75% agreement both sensors individually provided. This shows how a data processing method that uses the combined signals from different, less sophisticated sensors can greatly improve the measurement result. This parSYNC* is a mathematical model of the relationship between reference method and sensor responses non-linearly mapped across several time intervals (e.g., 3 seconds if the instrument is logging at 1 second resolution).

Figure 13D:
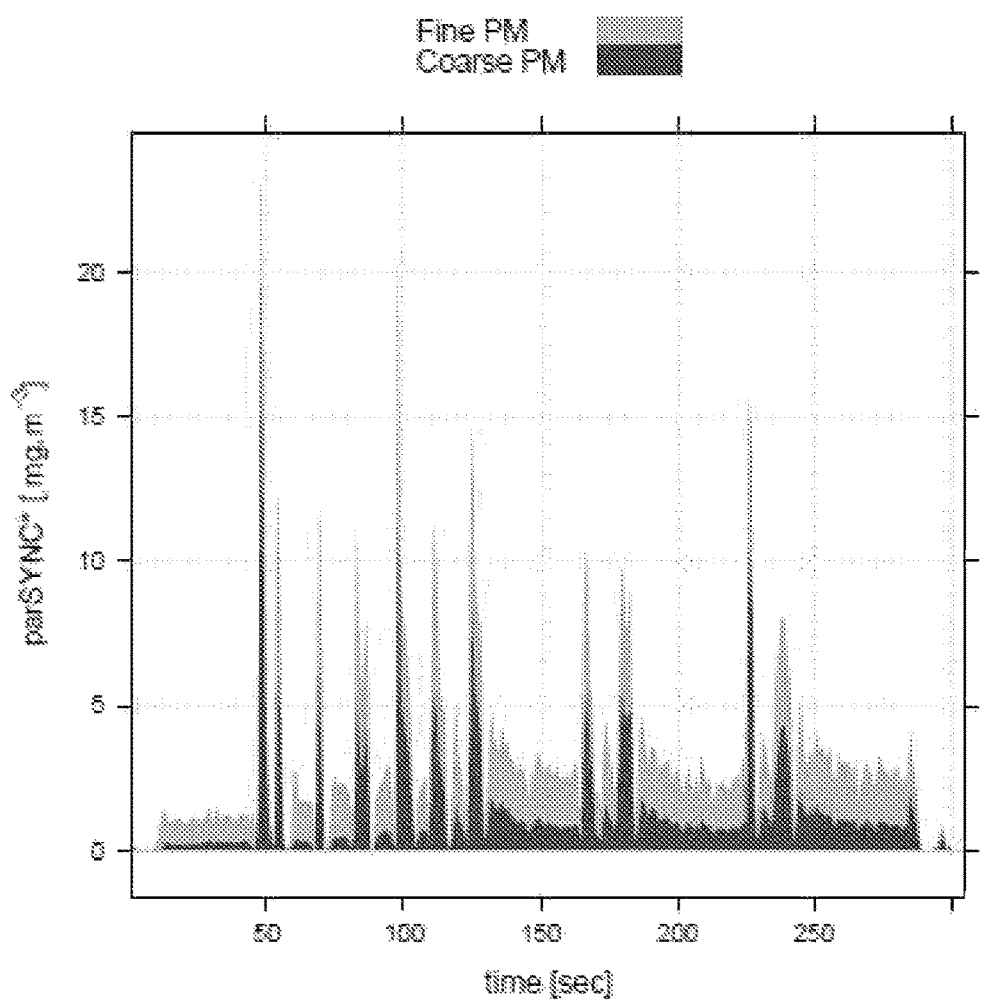

The ability of the multiple sensor technique to provide additional diagnostic information is illustrated using the example shown in FIG. 13D. Here, the fine/coarse split in the same vehicle exhaust particulate sample is estimated using a simple linear proportionality term. Fine particles equal (parSYNC*)×((ionization sensor measurement)/(sum of scattering, opacity, and ionization sensor measurements)), where parSYNC* represents the final, combined (multi-sensor) and post-processed output of the unit for a given sample or test.

Such a combination of performance and diagnostic information is presently not attainable in conventional portable systems because of the compromises or trade-offs required with respect to size, weight, power supply, or other factors to make a portable system, and the reliance on a single PM/PN measurement technique, which regardless of accuracy can only provide one dimension of information. Therefore, the totality of the multiple, dissimilar, in-line sensors can either be evaluated separately on their own merits (e.g. used as a "flagged" event), post-processed at a future date (utilizing a different/new metric set to accommodate for historical data sets in the future), or combined into one metric such as parSYNC* above based on a reference method, a secondary measure such as a pass/fail for a vehicle emission performance test such as the California Smog Check, or an arbitrary numeric scale on which such secondary measures can be evaluated. This latter concept is illustrated using the Particulate Synchronization Number (PSN) a weighted sum of sensor outputs, optimized to differentiate pass (low PSN values) and fails (high PSN values) relative to a pass/fail threshold.

An opacity sensor approach is generally responsive, robust, and well accepted. For example, it provides the basis of the SAE J1667 standard test. However, an opacity sensor approach is biased toward samples more heavily loaded with larger particles and black smoke, and is now widely regarding as an inexact and even unreliable measure of PM/PN for modern vehicles that tend to emit much finer material.

A scattering sensor approach is generally more amenable to emissions from modern vehicles. It is more sensitive to smaller particulate size fractions. Instrument configurations are robust and can be readily deployed in a similar fashion to existing opacity systems. However, it has limited sensitivity to the very finest particulate, a fraction that is becoming an increasing important component of vehicle emissions.

An ionization sensor approach is generally biased towards these smaller particles, but is not necessarily as responsive as optical/light-based sensors or as easily-deployed in more challenging sampling situations. This approach is also highly-sensitive to issues associated with water condensation.

An acoustic sensor approach, which may incorporate a frequency-based or particle counter approach, provides an alternative to traditional sensor methods, but may need to be carefully calibrated to routinely provide reliable data, which is an issue that would hinder its standalone use in many inspection vehicle approval schemes.

Such sensor advantages and disadvantages also enable a unique and specifically-arranged configuration. The embodiments disclosed herein ensure that each sensor is "seeing" the exact same sample parcel. As such, the sample chambers are laid out or plumbed in a linear (series), versus simultaneous (parallel), configuration. Thus, the sample chambers and sensors are serially connected in a linear arrangement. A sample will be transported from a first sensor to a second sensor to a third sensor and so on. Such a linear configuration can ensure that particles of the emissions sample pass through each sensor and the flow rate can be optimized to maximize the dwell-time sensitivity trade-off. Thus, the flow rate provides enough time in each chamber so each sensor can accurately measure the sample, but not so much time that the sample has a chance to change significantly with its surroundings to condense, degrade, decompose, or otherwise interact. Further, a power, heat, and water vapor management system in a compact space and in close proximity to the sample exhaust may be used to condition the sample to maximize the measurement accuracy and correctly distinguish the various PM/PN sample signature(s).

The system includes a PM/PN sensor cartridge comprised of multiple different and synchronized sensors, a computerized circuit controller board, a wireless duplex/transceiver, and a software system designed to combine the differing sample parcel signatures in real time. A pneumatic pump unit may be used to transport the sample into and out of each sensor chamber within the sensor cartridge. Other pump designs also may be used.

The power, heat, and water vapor management system of the device may be integrated in one sealed housing and chassis. Placement of the onboard battery/power unit, sample cartridge, main sample tubes, and other physical hardware in a single, compact space, and in close proximity to each other can ensure an optimal, stable, and constant temperature throughout all hardware components. Thus, the temperature in each of the sensors may remain approximately equal relative to the temperature in the other sensors at a given time, as the device's total mass temperature regulates to the ambient temperature plus the additional waste heat from the sample air over time (e.g., during testing). Temperature ranges for this device may be approximately −3° C. to 37° C., though other operating temperatures are possible. Maintaining an approximately equal temperature in each sensor avoids drawbacks of other designs that separate these components by both physical space and/or separate housings because the entire unit maintains the same approximately constant temperature while the sample travels through various sensors and pathways. The high temperature and temperature stability assists in significantly reducing the water vapor and condensation buildup that typically occurs in PEMS systems. Additionally, the physical design of the flow pathways can utilize gravitational assistance by creating peak and valley sample tube positions. This, in turn, enables water condensation to easily collect in the valleys and to be ejected without the use of pumps or other powered systems.

Software can be configured to integrate the raw data from the multiple sensors (such as three or more sensor time series) and can be used individually, in combination with each other and/or with other properties measured by onboard sensors (e.g., sample temperature and humidity), to provide measures or surrogate measures of different PM/PN metrics based on secondary calibration principles such as, for example, the comparison of at least one reference parameter measurement. The quantity within the exhaust sample can be the amount (e.g., mass, number of particles, concentration, etc.) of a known pollutant within the exhaust sample. The software can utilize mathematical relationships developed through comparison trials between the device's onboard sensors and several external, accepted testing methodologies and standards. These mathematical relationships have been converted into the software code so as to provide the user with the appropriate, seamless comparison data that corresponds to various laboratory standards.

Further, the targeted parameter can be any property of PM/PN (e.g., a soot metric such as Soot Number, or a PM or PN as measured by a particular instrument) and the associated surrogate can be produced by mapping sensor inputs as, for example, a non-linear function of the individual sensor signals, ratios of either the combined signals, or a direct signal from one or more sensors.

The device can obtain sequential/linear measurements of the sample parcel utilizing multiple measurement capabilities such as opacity, light-scattering, ionization, electrostatic precipitation, and/or acoustic technique(s). At least one measurement, such as three or more different measurements, can be used as the basis for mapping sensor responses onto a reference measurement. For example, three, four, five, or six sensors can be used together. Other numbers of sensors are possible. In an instance, two different acoustic techniques, for example, can be used together in the three or more sensors. In another instance, two light scattering sensors are used, each having a different color laser.

In some instances it may be preferable to utilize a blue laser to avoid potential heat interference associated with exhaust flow common with red lasers. Red laser light sources are higher energy devices than blue light sources. A blue laser also may allow for a shorter measurement distance.

Use of the combined PM/PN measurements can provide a lighter device with a smaller footprint that is cheaper to manufacture.

An embodiment of the device can utilize at least three of the following: a small-scale opacity reading with a laser light wavelength; a miniature laser light scattering measurement; a compact ionization measurement; and an acoustic chamber. Other combinations of sensors are possible.

When combined and harmonized, these three or more individual PM/PN measurements provide a more accurate view of PM/PN through triangulation by responding uniquely to the chemical and physical variety commonly found in any PM/PN sample. Furthermore, in instances where comparisons have already been made, these combined PM/PN measurements compare favorably to current industry opacity meter, laser-light scattering, and other industry-accepted measurement techniques.

Different embodiments and/or variations may contain the following configurations: a module for gaseous pollutant measurement (additional baseline methodology to establish a secondary ratio based on non-PM/PN pollutants); a secondary light scattering sensor at a differing frequency to further delineate real time events, based on additional input; and/or hardwired power and data harness for the simultaneous logging of other data sources (for example, OBD2 or CAN data from the vehicle the device is used in combination with for PEMS applications).

Figure 2:
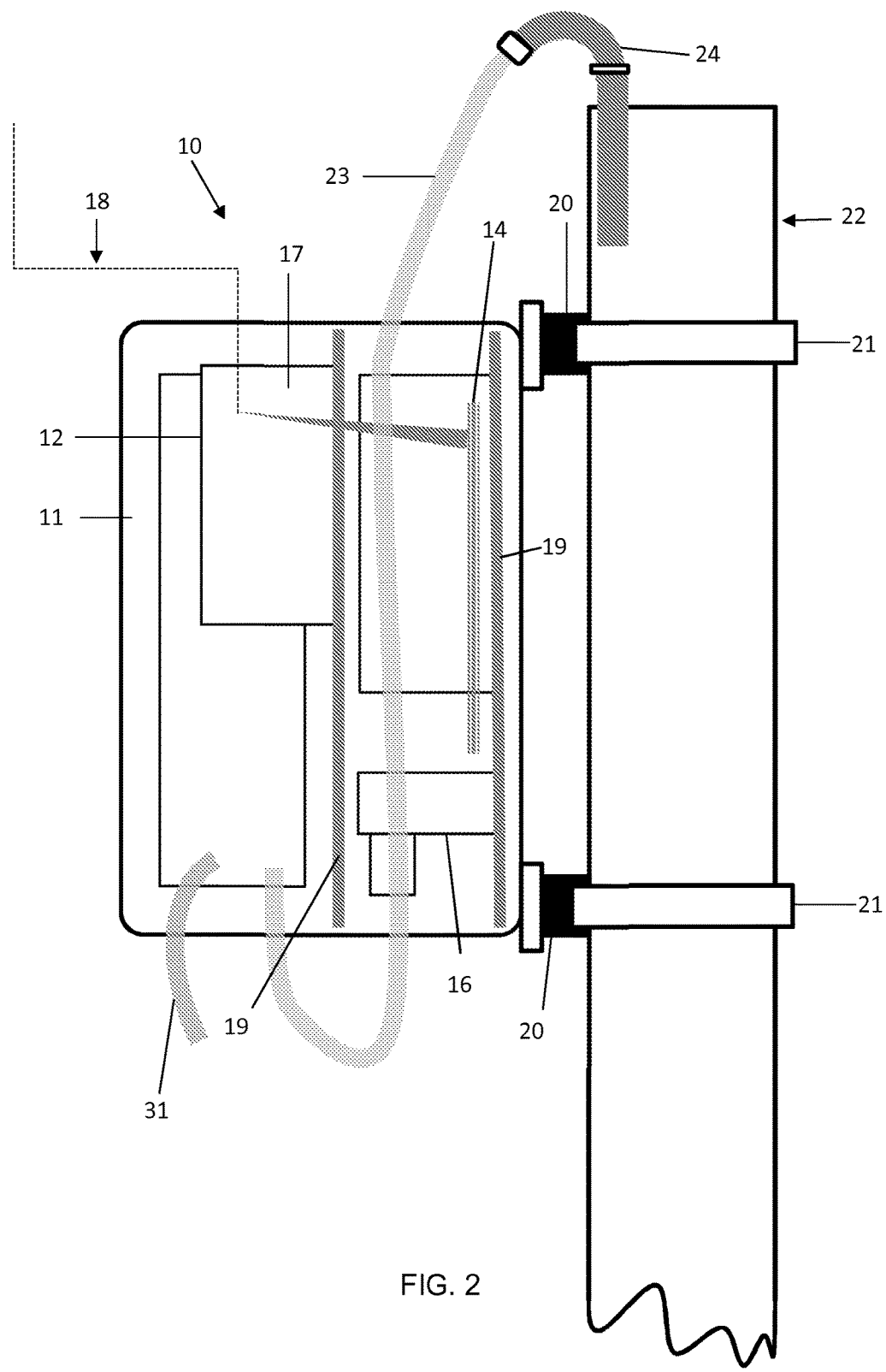
FIG. 2 is a schematic of the disclosure shown in FIG. 1 in a first configuration mounted to an exhaust stack in accordance with the present disclosure.

The system disclosed herein and illustrated in FIGS. 1 and 2 provides an improved apparatus for sensing PM/PN emissions from exhaust at point 22 comprised of a synchronized set of differing PM/PN sensors in a system 10 configured to communicate in a wireless 18 or wired manner with a processing unit 60, which can also obtain engine data via an engine data unit 70 connected either in a wireless 50 or wired configuration. The engine data unit 70 logs engine management data accessed and used by the vehicle's engine management system. These engine management data use the speed of the engine and engine manifold pressure (RPM and MAP data sets) and other engine diagnostics to calculate properties such as the exhaust gas flow rate within the exhaust system. The engine data unit 70 can also access the vehicles speed (Hall sensor output) or incorporate a global positioning system (GPS) vehicle location and speed data, which can be used in combination with exhaust emissions data to more comprehensively characterize the relationship between vehicle activity and total emissions.

In an example, the cartridge of the system 10 has an exterior polycarbonate/plastic shell approximately 193× 117×57 mm in dimension, which is waterproof, airtight, sealed, and self-contained. Other shell materials or sizes are possible. The shell or housing contains a multi-channel sensor device. The cartridge of the system 10 may weigh less than 0.5 kg and may have three main orifices: a sample flow inlet, a sample flow outlet, and an electronic coupler which provides power to the sensors as well as duplexing capabilities to control the internal sensors and to relay voltages and/or signals. The cartridge can be designed for use with quick release friction-and-pressure coupling. The cartridge coupling array also may utilize shock-absorbing materials (e.g., rubber, neoprene, etc.) and a tension design to create a shock-resistant framework or "cradle" to separate the cartridge array from the main internal housing. These features all contribute to a singular, easily-replaceable cartridge. A field-replaceable PM/PN cartridge greatly reduces present down-time associated with repairing a bad sensor. The cartridge in system 10 can provide for a new sensor replacement while the old/bad sensor is repaired at a better time and/or location.

The source may be comprised of an internal combustion engine 5 and include an exhaust tailpipe or stack at point 22. The system 10 may comprise a sample probe 24 and sample tube 23 extending from the inlet port of the system 10 into the exhaust tailpipe or stack at point 22. The source may be a mobile internal combustion engines for passenger vehicles, buses, light duty trucks, heavy duty trucks, motorcycles, off-road vehicles, non-road vehicles, farm equipment, construction equipment, aircraft, locomotives, or water vessels. The source(s) may also consist of generators, drainage and irrigation pumps, or compressors. The source(s) also may be other devices that produce emissions. In an example, a distance between the tailpipe exhaust and the device inlet is 1 m, which ensures that the device is as close to the source as possible so as to optimize sample heat and minimize condensation. The sample tubing in this example is a variation of a high heat silicone with a 3 mm diameter.

The PM/PN exhaust sensor array cartridge 11 may employ multiple, synchronized techniques from a group consisting of, but not limited to: laser light opacity, light scattering, particle ionization, particle acoustic measurement, and electrostatic precipitation. Electrostatic precipitation is a technique whereby particles are positively charged and measured on oppositely charged plates. Some of these various configurations are disclosed in FIG. 3 and FIG. 4. Of course, other types or sensors or sensor designs also may be used.

In an embodiment, the system 10 uses laser light opacity, laser light scattering, and particle ionization sensors. When combined, these three sensors compare well with presently accepted and recognized individual surrogate standards and also combine into an improved triangulation of data that allows speciation between various particulate sizes. Other combinations of sensors are possible and may provide equally improved results.

A combination having two, three, or more of the same type of sensor also may be used. These three sensors of the same type may have different tuning, configurations of lasers, or be operated at different frequencies. Thus, while different measurement methods in different types of sensors may be used, different parameters or properties in the same type of sensor also may be used.

The processing unit 60 may have a microprocessor configured to provide emission data as a function of measurements from the PM/PN sensors and the engine data unit 70. The target measurement of the pollutant may include, but not be limited to particulate mass, number, size, striation, weight, etc. The combined relationship(s) and ratio(s) of the multiple, synchronized PM/PN sensor outputs, when compared to an external reference such as a standard laboratory benchmark method, may be used to impute a surrogate measurement comparable to that of the laboratory reference from the system 10.

The power source may comprise a battery 12 with an external charger port. The battery 12 may be a lithium ion battery. However, other batteries that provide a small size or weight, durability (e.g., drainage and recharge capacity, hot/cold temperature performance, other environmental condition performance, etc.), and sufficient high-density power storage capacity or an external power supply may be used.

Referring now to the figures, and specifically to FIG. 1 and FIG. 2, this system 10 provides an improved PM/PN emissions measurement system depicted as including an exhaust probe 24 attached to an exhaust stack or tailpipe at point 22. The system 10 may be configured to hardwire or wirelessly 18 communicate with a processing unit 60 which may also be obtaining engine data via an engine data unit 70 connected either in a wireless 50 or wired configuration. The system 10 also has an analog-to-digital conversion unit and wireless communications device 14 (e.g., a Bluetooth device), a pump 16, a transmitter 17, a baseplate 19 used to attach specific electronic components, unit connections 20, and exhaust clamps 21. The baseplate 19 may be fabricated of high-tensile polycarbonate in an embodiment. Moisture-sensitive electronic components and less moisture-sensitive electronic components may be positioned on opposite sides of the baseplate 19. Thus, the baseplate 19 can serve as a moisture barrier. The unit connections 20 may be corrosion-resistant material such as stainless steel, brass, chrome, high-heat silicone, or other material. The unit connections 20 may be configured to facilitate an air-tight seal while transferring the sample from the vehicle tailpipe exhaust into the sample tube 23, through the sensor cartridge, through a pump, and exhausted out of the device outlet. The exhaust clamps 21 also may be made of corrosion-resistant material such as stainless steel, brass, chrome, high-heat silicone, or other material. The exhaust clamps 21 are configured to connect the cartridge 11 proximate to or on the vehicle exhaust. The sample probe 24 is connected to the vehicle exhaust at point 22 using, for example, a clamp, adhesives, another mechanical device, or some other fastening method. The analog-to-digital conversion unit and wireless communications device 14 also may be separate units in an embodiment. Although a Bluetooth communications device is mentioned, other communication devices such as Ultra WideBand (UWB) or IEEE 802.11af (White FI) could also be used.

Figure 3:
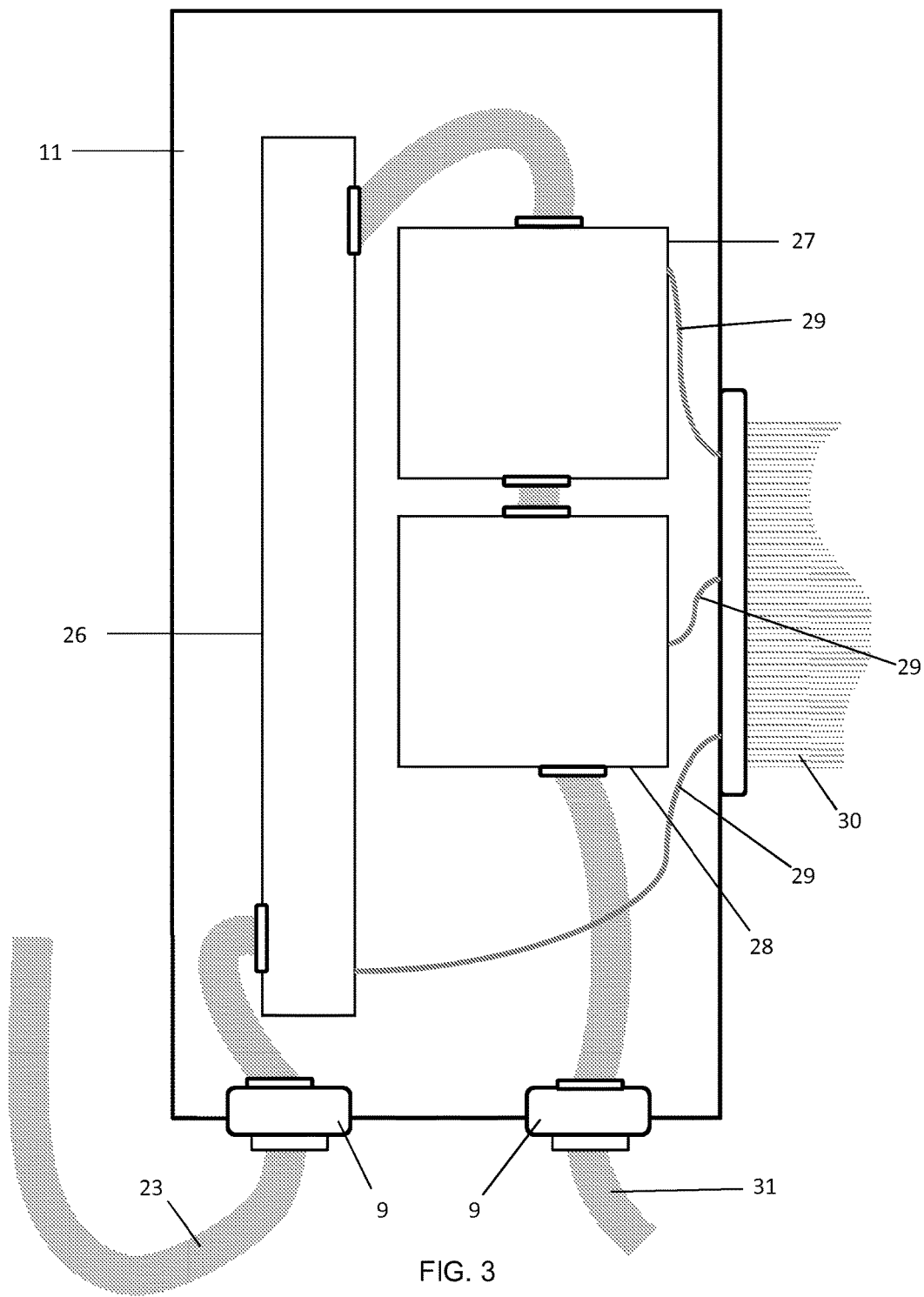
FIG. 3 is a top perspective view of the PM/PN sensor cartridge shown in FIG. 2 in a first configuration.
Figure 4:
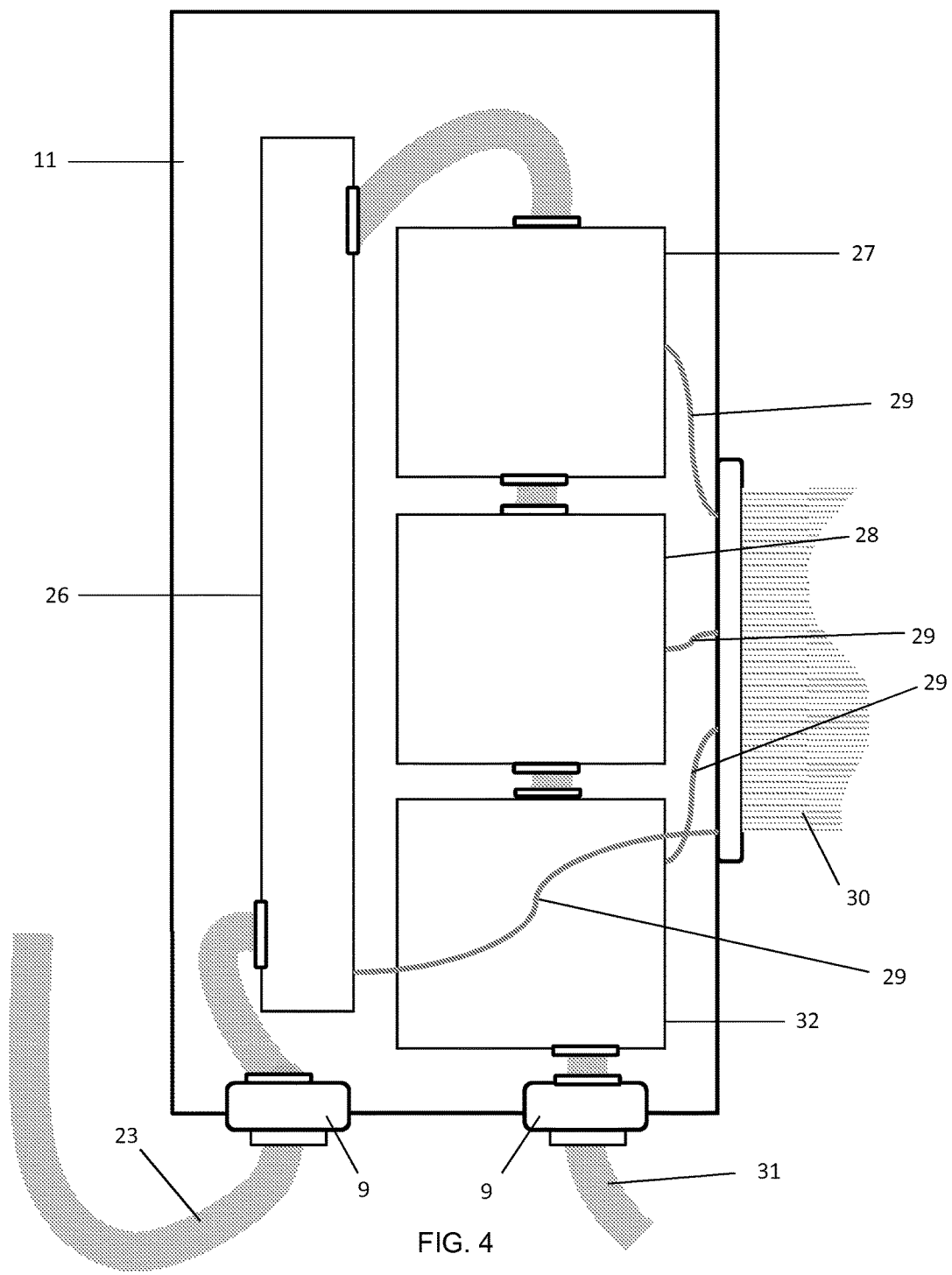
FIG. 4 is a schematic of the PM/PN sensor cartridge shown in FIG. 2 in a second configuration.

The PM/PN exhaust sensor array cartridge detailed in FIG. 3 and FIG. 4 employs a specific linear sequence of sensors 26, 27, 28, 32 under negative pressure. There is a sample inlet 23 and outlet 31 through a fitted seal 9. Each seal 9 may be, for example, a corrosion-resistant brass and/or stainless steel fitting that can accommodate fitted and sized quick connect/disconnect tubing. Each individual sensor 26, 27, 28, 32 is electronically connected via an individual wiring connection or connections 29 which supply power and/or relay specific voltage readings to the main wiring harness 30. The main wiring harness 30 can be coupled and uncoupled via a plug-in connector. It should be noted that the entire sensor cartridge assembly 11 can be designed to be removed quickly and efficiently, and replaced in its entirety with an identical cartridge 11.

Turning back to FIG. 2, the system 10 includes at least three separate PM or PN sensors. The PM or PN sensors are connected to a processing unit 60, which includes a processor and software configured to estimate an overall PM/PN value for an exhaust sample based on PM/PN parameters or signatures associated with the exhaust sample. In an implementation, only a single sensor output and an associated calibration would be required to provide a PM or PN estimate. However, three or more PM/PN sensor outputs are synchronized with each other and integrated or combined using, for example, a linear or non-linear function to map the individual sensor outputs into a singular surrogate number (based on externally accepted measurement standards) or a "unified property" and more accurately describe the PM/PN characteristics of the exhaust sample. At least one exhaust parameter may include a proportionality factor determined, at least in part, based on amounts of PM/PN within other previously sampled and calibrated PM/PN exhaust. A weighted linear integral factor, or a non-linear integral factor may be used instead of a proportionality factor.

The sensors are in a singular cartridge 11, which is attached to a flexible, shock-resistant suspension band. Quick-disconnect fittings and electronic ribbon connectors can expedite replacement of the cartridge 11 and/or unit 10. The cartridge 11 can be mounted within the unit 10, which can be mounted proximate a source of the exhaust sample. This is typically in a high-vibration or adverse ambient condition. The cartridge 11 and/or unit 10 can be resistant to dust, liquid water, and severe weather.

Figure 5:
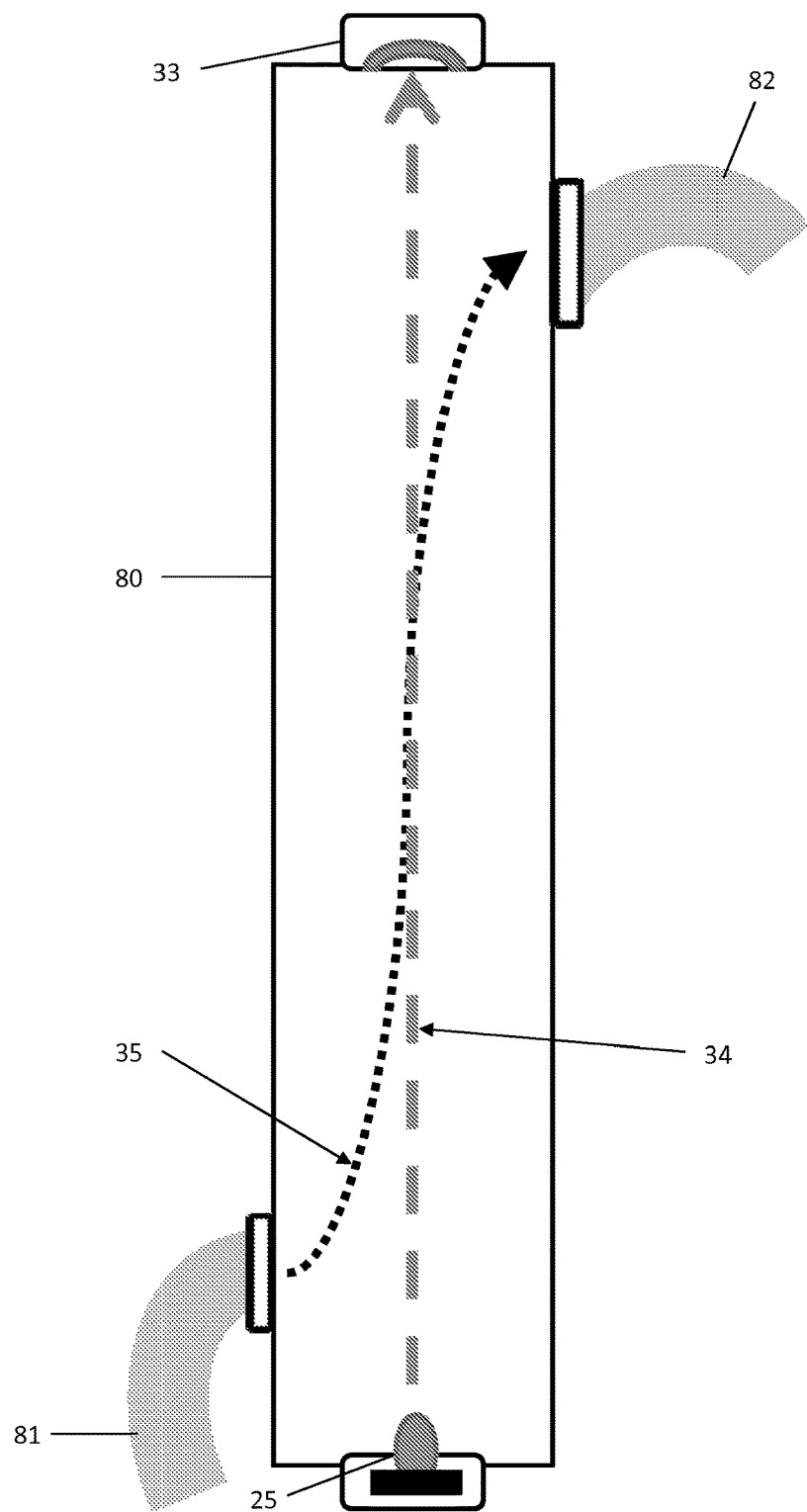
FIG. 5 is a schematic of an embodiment of a laser light opacity sensor.
Figure 8:
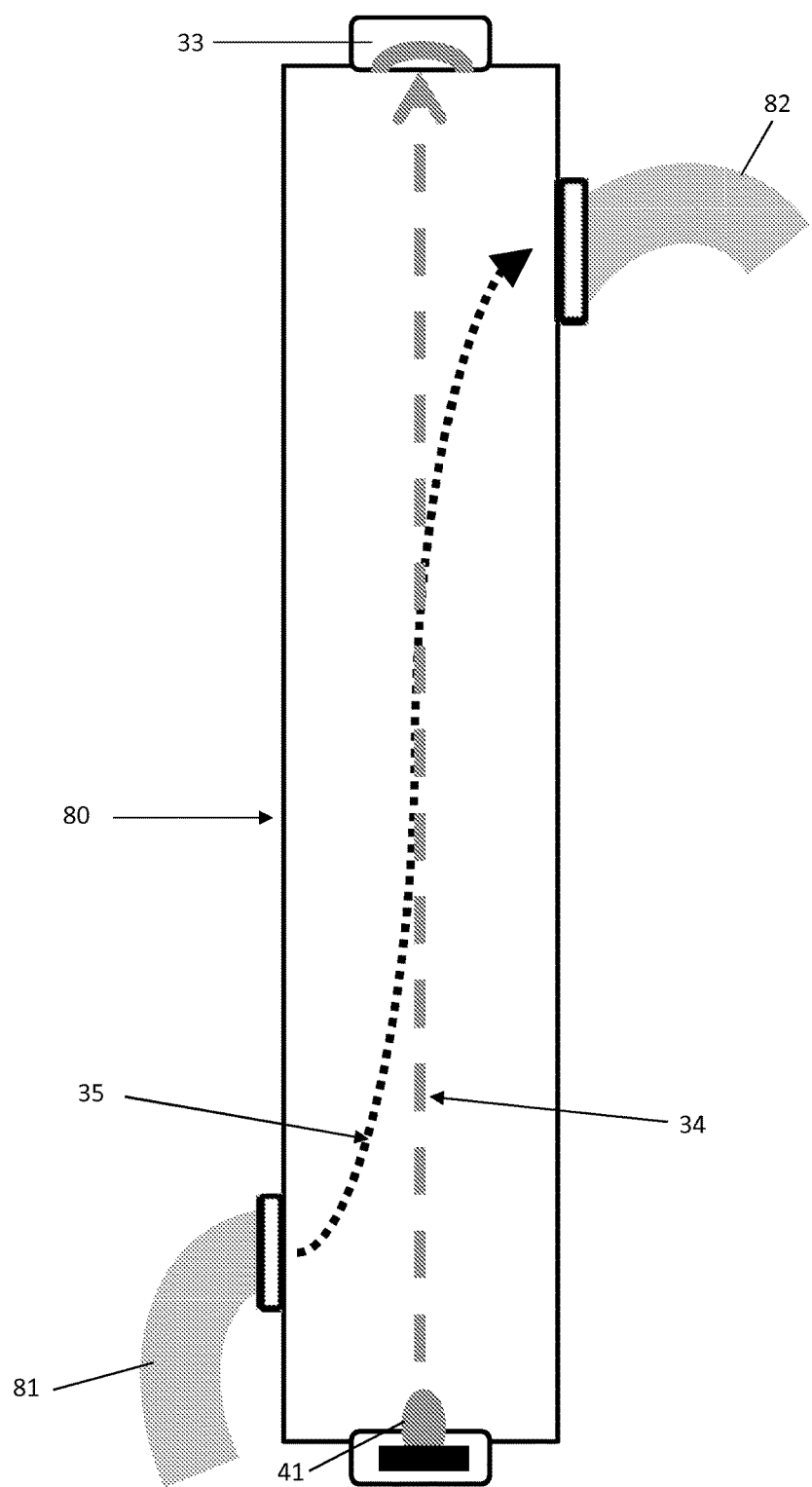
FIG. 8 is a schematic of another embodiment of a laser light opacity sensor.

The opacity sensor designs 80 in FIG. 5 and FIG. 8 have been simplified to abridge the configuration. This translates to a reduction of weight, space, and power usage with an acceptable or negligible impact to results. The sample flow 35 enters the sensor 80 through inlet 81 and the amount of particulate proportionately blocks the laser 25 as the path of laser light 34 travels to, and is detected by, the photoreceptor 33 before the sample exits the sensor 80 through outlet 82. A blue laser 25 may be used, as seen in FIG. 5, but an alternate laser 41 (e.g., red laser, green laser, etc.) is represented in FIG. 8 as a potential alternative. The exact type of color/emission frequency and range, emission strength, path length, or number of opacity sensors may be varied to maximize the degree of PM/PN characterization for a given sample.

Figure 6:
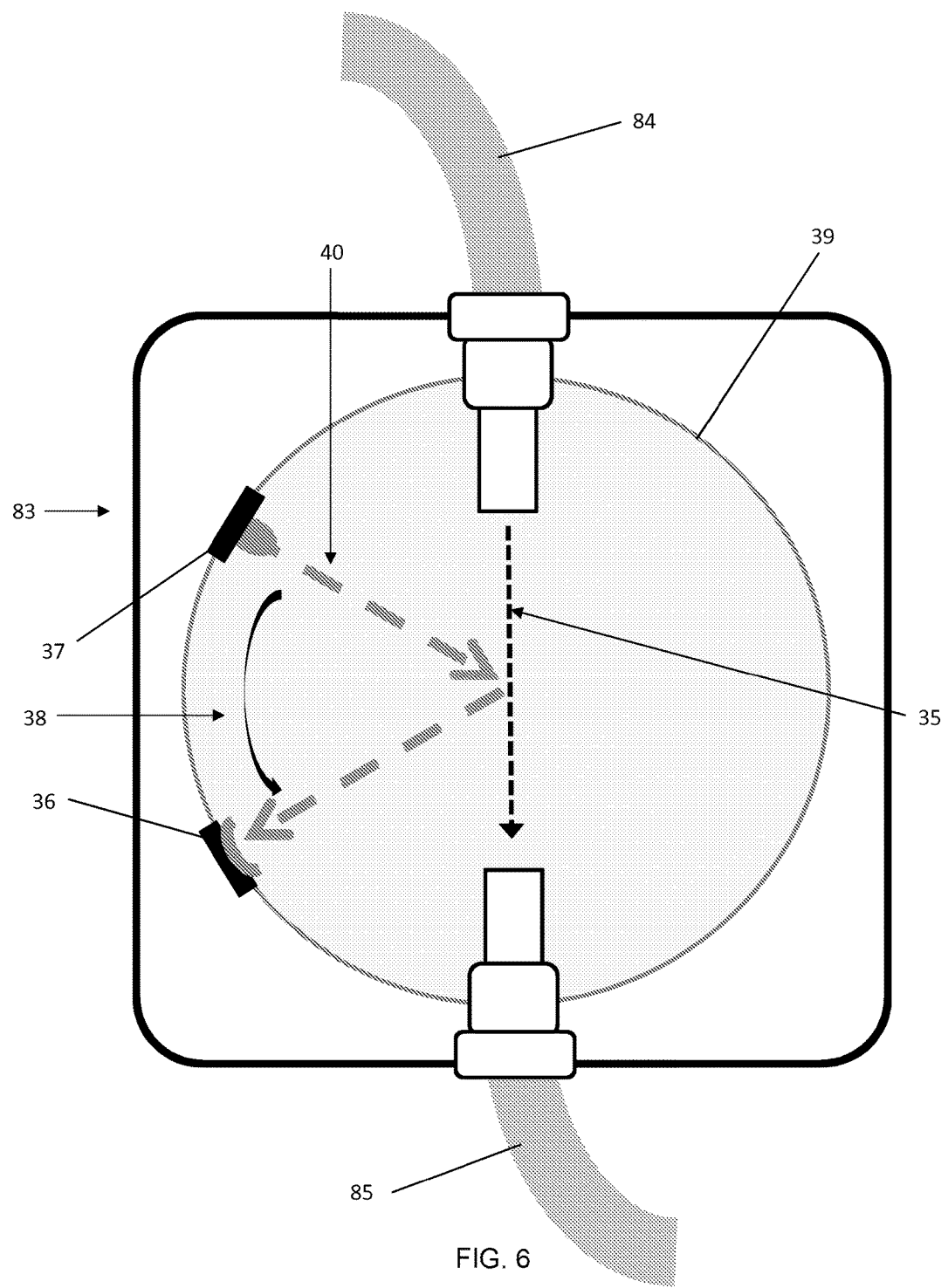
FIG. 6 is a schematic of an embodiment of a light-scattering sensor.

The light scattering sensor 83 in FIG. 6 has also been simplified to abridge the configuration. This translates to a reduction of weight, space, and power usage with an acceptable or negligible impact to results. The sample flow 35 enters the sensor 83 through inlet 84. A laser light source 37 projects a laser 40 at the sample flow 35 pathway in the external protective and airtight membrane 39. The amount of particulate proportionately reflects off of the individual particle surfaces at an optimal angle 38 and the amount of scattered light is detected by a photoreceptor 36 positioned to measure light reflected from the laser path 40 while the sample flow 35 exits the sensor 83 through outlet 85. A red laser has been represented, but alternate lasers (e.g. blue, green, etc.) also may be used.

Figure 7:
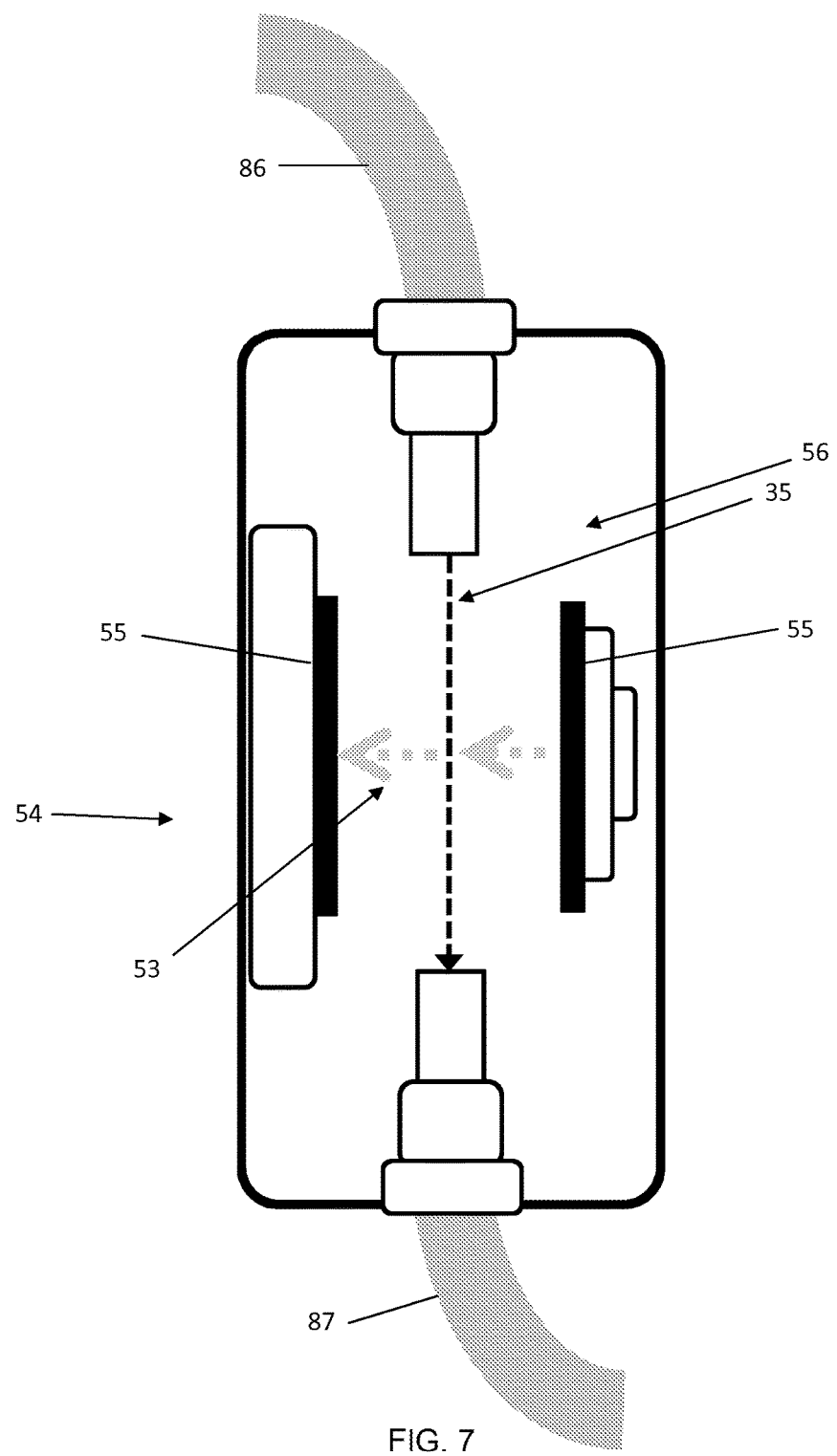
FIG. 7 is a schematic of an embodiment of an ionization sensor.

The ionization sensor 54 in FIG. 7 has also been simplified to abridge the configuration. This translates to a reduction of weight, space, and power usage with an acceptable or negligible impact to results. The sample flow 35 enters the sensor chamber 56 through inlet 86 and an ionization system 55, which may use radiation 53, electrons, RF power, or other mechanisms, positively or negatively charges particles as they enter the sensor chamber 56. The charge consumed in charging particles in the sample as it passes through the sensor chamber 56 creates a measurable voltage or current change, which is detected by the ionization system 55 before the sample exits the sensor chamber 56 through outlet 87.

Figure 9:
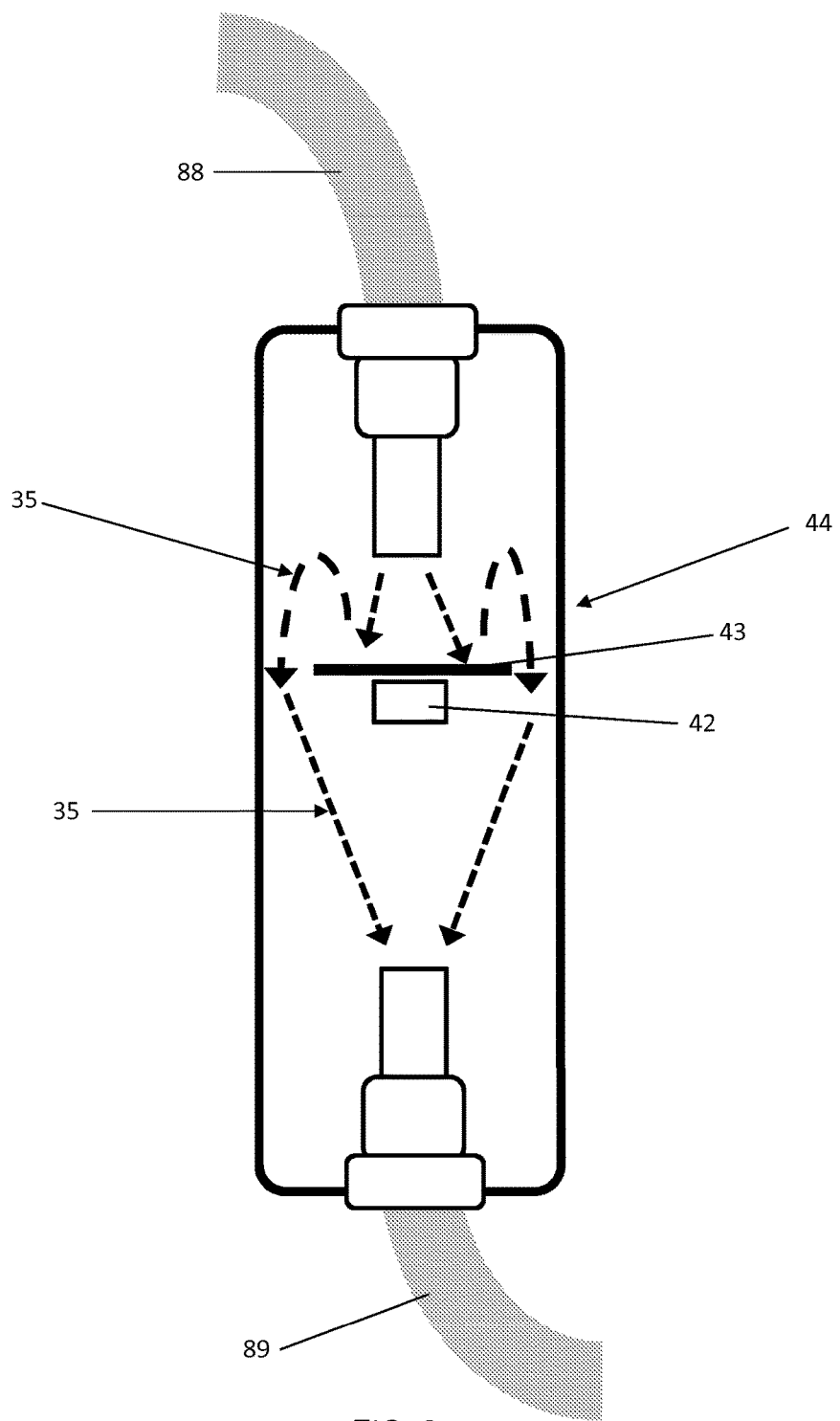
FIG. 9 is a schematic of an embodiment of an acoustic sensor.
Figure 10:
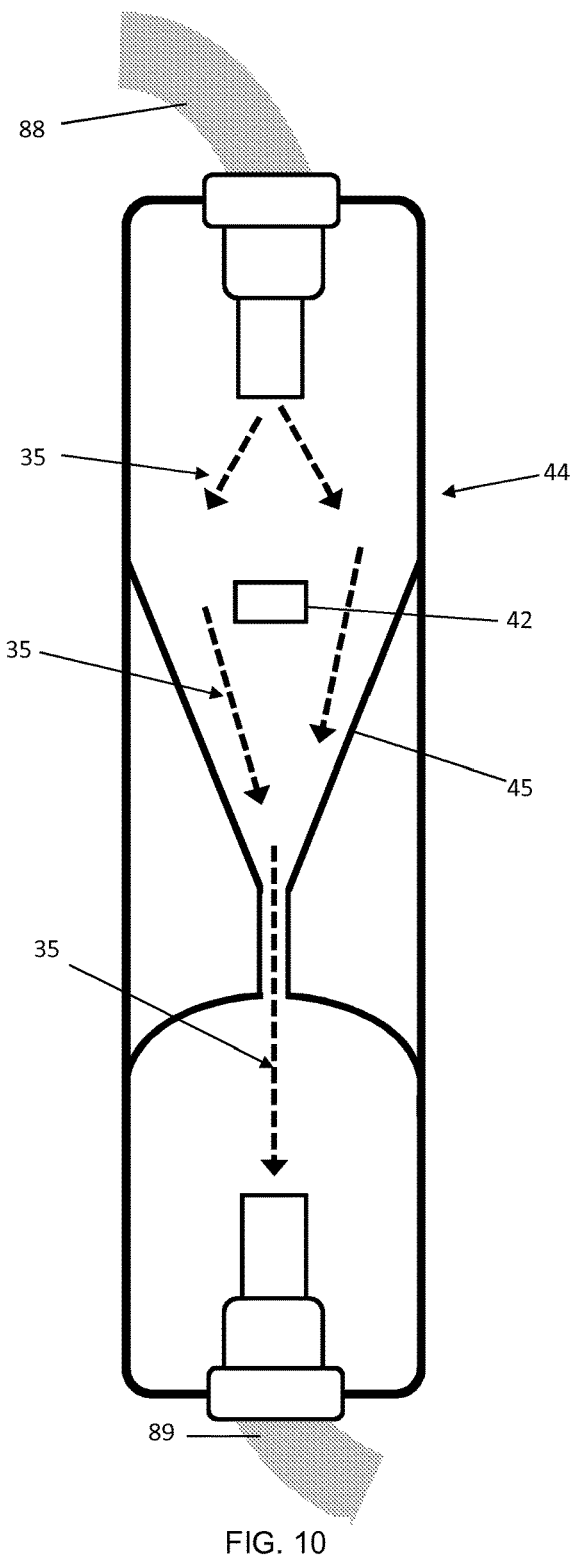
FIG. 10 is a schematic of another embodiment of an acoustic sensor.

The acoustic sensors in FIG. 9 and FIG. 10 are two embodiments of a sensor that employs the detection of sounds and/or frequency variations. FIG. 9 features acoustic particle detection whereas FIG. 10 employs acoustic frequency change detection. In both examples, the sample flow 35 enters through inlet 88 and exits through outlet 89 in the acoustic chamber 44. Each acoustic sensor utilizes a highly sensitive microphone 42. However, the embodiment of FIG. 9 utilizes a high-tensile membrane 43 to detect particles the sample flow 35 as they collide with the membrane 43. The embodiment of FIG. 10 employs a decreasing funnel 45 which induces frequency pitch changes as the flow of particles in the sample flow 35 becomes more turbulent as the particles are forced into an increasingly narrow pathway.

The sensors in FIGS. 5-10 are examples of the sensors 26, 27, 28, 32 in FIGS. 3-4. The exact combination, order, or configuration of the sensors in FIGS. 5-10 can vary. The inlets and outlets in FIGS. 5-10 can connect between sensors, to the inlet 23, or to the outlet 31. Fluid can flow through the inlets and outlets in FIGS. 5-10.

Figure 11:
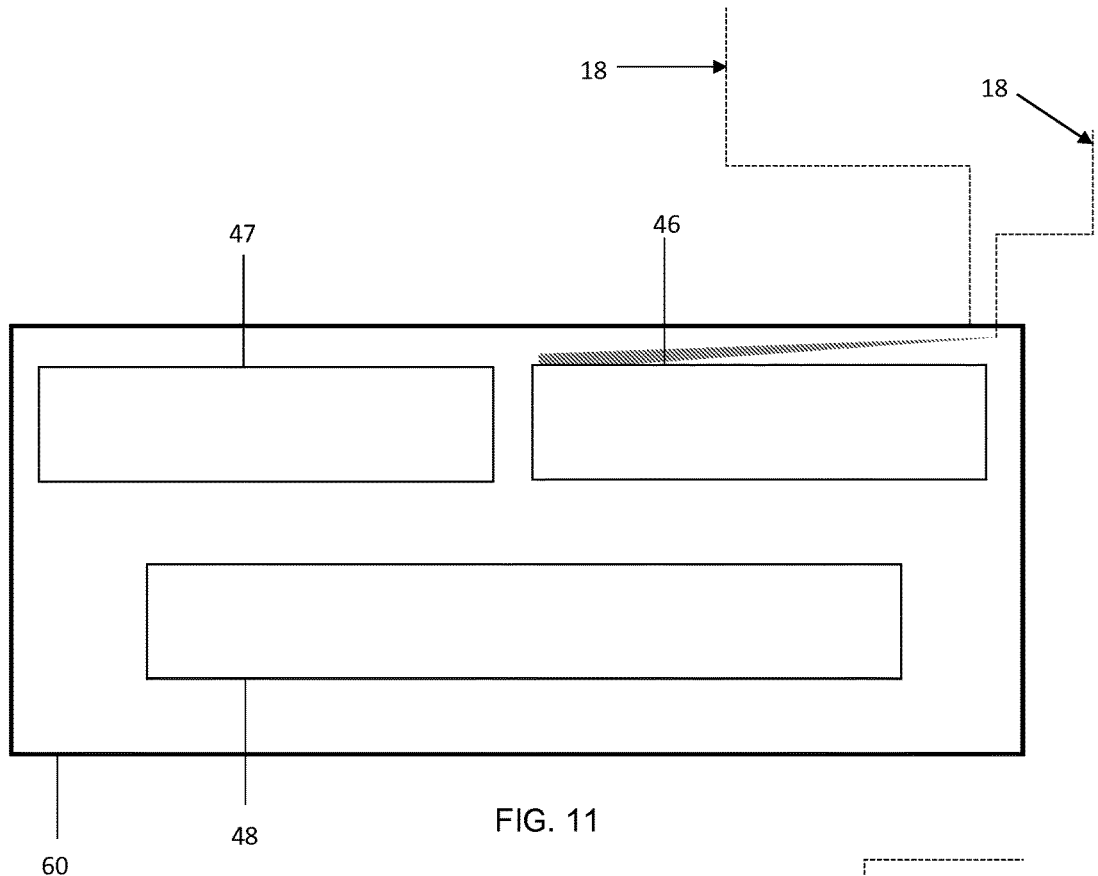
FIG. 11 is a schematic of an embodiment of the processing unit shown in FIG. 1.

The system 10 in FIG. 2 utilizes a transmitter 17 to communicate data to a processing unit 60 (which may be a "smart device") in a wired or wireless 18 manner, which is illustrated in FIG. 11. The measurement and status data are received via a transmitter/receiver 46 and outgoing instructions (e.g., calibration instructions, equation modifications, etc.) are sent 18 via a duplexing capability. The processing unit 60 has a transmitter/receiver 46, a processor 47, and data storage medium 48, with additional input from a user.

The processor 47 can initiate a channel configuration, using transmitter/receiver 46, that tells the analog-to-digital conversion unit and Bluetooth communications device 14 how many and which ports on the analog-to-digital conversion unit and Bluetooth communications device 14 will be used for measurement. The channel configuration also includes specifications such as voltage or current ranges, speed of data acquisition (i.e., how many samples per second), the size of the buffer where data is stored temporarily, and the duration of data acquisition (e.g., one time or continuous). After the analog-to-digital conversion unit and Bluetooth communications device 14 is configured, the processor 47 will begin acquiring measurements based on a user "start" command. The processor 47 continuously watches the transmitter/receiver 46 and when data is available, the processor 47 will read and process the data and thereafter save the results to a file on a storage medium 48, such as hard drive, flash memory, or other memory device. The processing unit consists of computing hardware and a graphical user interface (GUI). The raw voltage signals generated by the system 10 are processed and presented as individual PM/PN measurements for each sensor and an overall triangulated value. Other data that are received from the system 10 could be temperature, flow, and humidity measurements. The processor 47 also can communicate with engine data device 70 using the transmitter/receiver 46. Depending on the hardware configuration, the transmitter/receiver 46 in processing unit 60 may be common for communication with the system 10 and engine data device 70.

In an another embodiment, at least part of the processing unit 60 is inside the system 10. This may utilize a real-time operating system (RTOS) and the appropriate processor 47 so that the controlling of data acquisition and computing of results can occur at the data acquisition point. This embedded processing unit 60 may have an onboard data storage medium 48 and can transmit data wirelessly to another processing unit (not illustrated), which will be external and can have real-time visual update. In this case, a loss of Wi-Fi, Bluetooth, or other wireless signal does not mean a loss of data, but merely the loss of visual updates of the data that is being stored by the onboard computer embedded inside the system 10. This alternate embodiment also may provide multi-day, unattended data acquisition. The system 10, can be powered up and down simultaneously with the engine.

Figure 12:
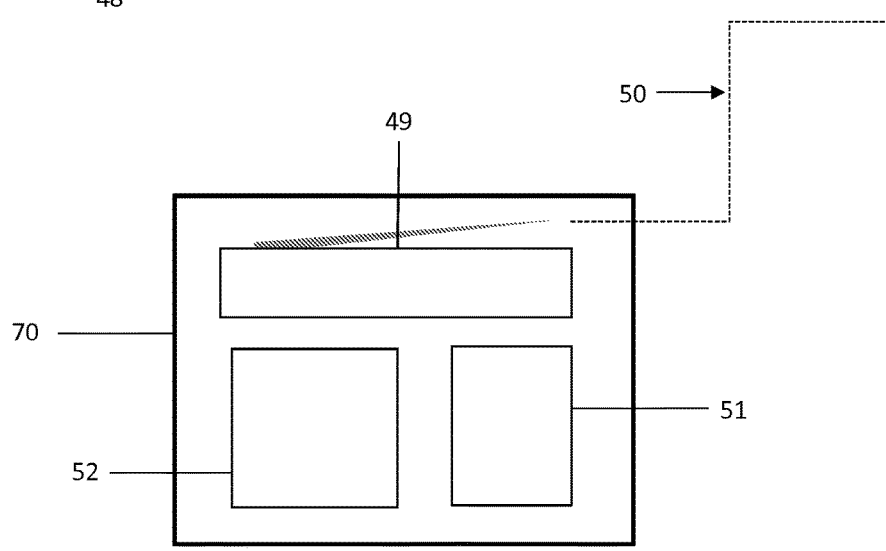
FIG. 12 is a schematic of an embodiment of the wireless engine computer interface unit shown in FIG. 1.

An additional source of data illustrated in FIG. 12 may be obtained from the engine source via a wired or wireless engine data device 70 by obtaining either engine control unit data or by temporarily or permanently placed engine sensors. The data is obtained via transmitter/receiver 49 and processed via an onboard computer 52. The engine data device then transmits the process engine data either using a hardwired connection or wirelessly 50 using the transmitter/receiver 49. In an example, the engine data device 70 can also have onboard storage 51 that creates a real-time backup of the data being received and transmitted. The engine data device 70 can connect to an engine via sensors or to an onboard engine computer.

Figure 14:
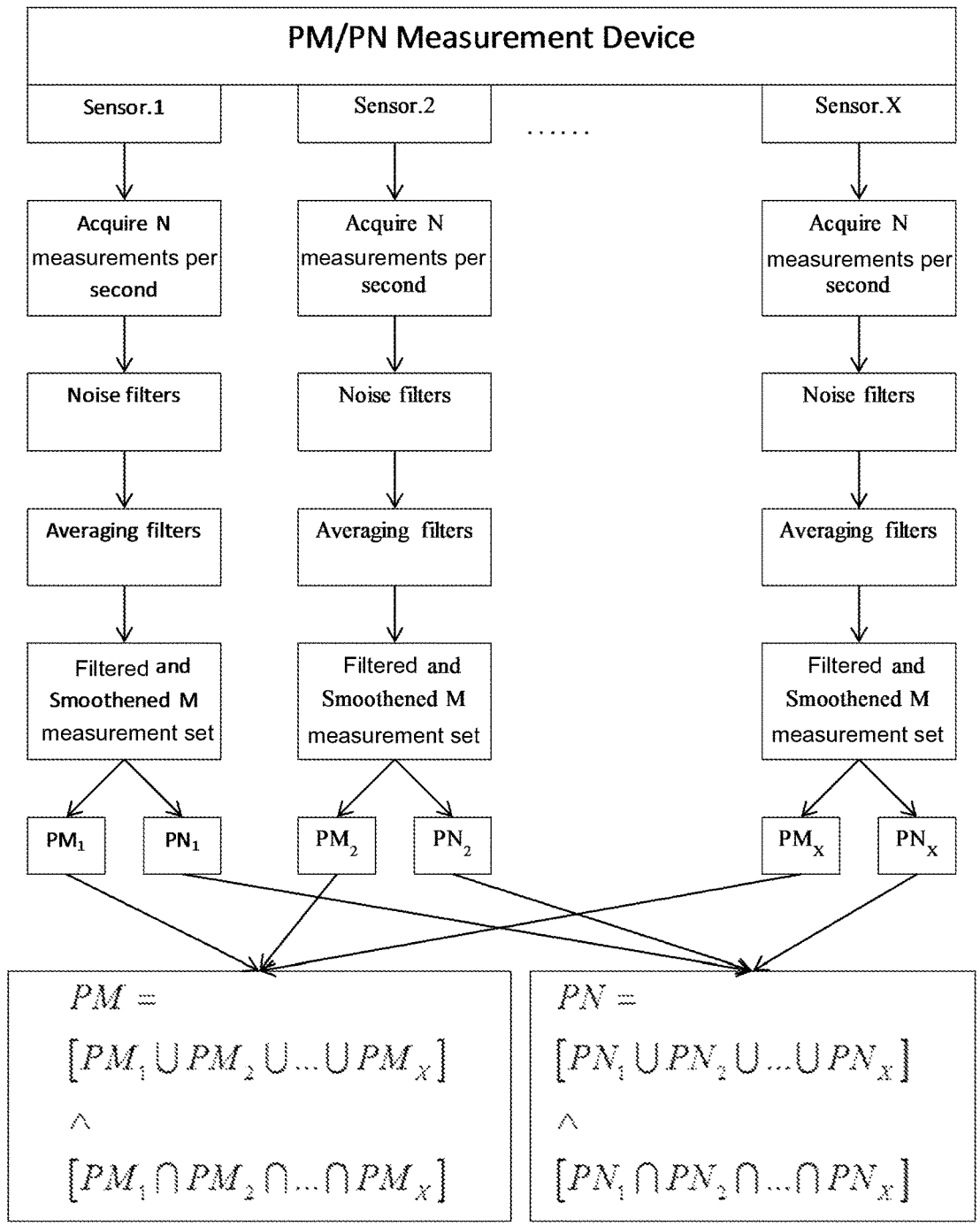
FIG. 14 is a flowchart illustrating an embodiment of software operation in accordance with the present disclosure.

The software design is demonstrated through the concepts of unions and intersects as applied to the field of set theory, as shown in FIG. 14. Each sensor is considered to be a set, one that reflects a certain space in the overall measurement of PM/PN. The function of the software is to combine these sets based on logical constructs.

Each sensor is "polled" at high speed to acquire, for example, thousands of raw data measurements per second. The raw data measurements from each sensor, which may be voltage or current readings, are subjected to analog filtering and smoothening to remove artifacts of electrical disturbances. This process is typically accomplished using a conventional signal filtering methods (e.g., a Kalman, Butterworth, or Elliptic filter or other similar noise reduction strategy). This causes the initial raw N measurements to be reduced to M measurements. The "cleaned" measurements from each sensor are then converted to silos of PM/PN measurements. Thus, for a three sensor configuration, there will be three measurements each of PM and PN. Potentially none of these is fully correct. These individual "incomplete" measurements are combined to provide a more complete and more accurate estimate of PM and PN.

Continuing the set field analogue, the process of combining individual PM and PN estimates is based on unions and intersects. The union function defines the overall space and increases the observability of PM and PN estimates during transient operation of the vehicle. The intersect function or triangulation term can be considered to multiplex or summarize description of the multidimensional entity indicated by the three synchronized sensor outputs.

While specific sensor designs have been disclosed herein, other variations or embodiments of the sensors also may be used.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. An emissions measurement system comprising:
   an emissions sample inlet;
   at least three sensors connected to the emissions sample inlet, wherein the sensors are sequentially connected in a linear arrangement and wherein each of the at least three sensors is configured to perform a different measurement of a sample;
   an emissions sample outlet connected to the at least three sensors;
   a sensor cartridge defining the emissions sample inlet and the emissions sample outlet, wherein the sensors are disposed within the sensor cartridge between the emissions sample inlet and emissions sample outlet;
   a sample probe that is fluidically connected to the emissions sample inlet; and
   a battery disposed in the sensor cartridge that is configured to provide power to the sensors.

2. The emissions measurement system of claim 1, wherein each of the sensors is selected from the group consisting of a laser light opacity sensor, a light scattering sensor, a particle ionization sensor, a particle acoustic measurement sensor, and an electrostatic precipitation sensor.

3. The emissions measurement system of claim 1, wherein the sensors comprise a laser light opacity sensor, a light scattering sensor, and a particle ionization sensor.

4. The emissions measurement system of claim 1, wherein one of the sensors is a laser light opacity sensor and wherein the laser light opacity sensor is configured to use a blue laser.

5. The emissions measurement system of claim 1, wherein the sensors are configured to be synchronized.

6. The emissions measurement system of claim 1, wherein a temperature in any of the sensors is equal thereby reducing water vapor and condensation buildup.

7. The emissions measurement system of claim 1, wherein the sensor cartridge further comprises shock absorbing materials disposed in the sensor cartridge.

8. The emissions measurement system of claim 1, wherein the sensor cartridge is configured to be connected to an exhaust of an internal combustion engine.

9. The emissions measurement system of claim 1, further comprising a processing unit wirelessly connected to the sensors.

10. The emissions measurement system of claim 9, wherein the processing unit is configured to provide results based on data provided by the sensors.

11. The emissions measurement system of claim 9, wherein the processing unit is configured to triangulate the data provided by the sensors.

12. A method of measuring emissions comprising:
    directing an emissions sample into an emissions sample inlet defined by a sensor cartridge;
    linearly transporting the emissions sample through at least three sensors in the sensor cartridge, wherein each of the sensors is configured to perform a different measurement of the emissions sample, and wherein the sensors are powered by a battery disposed in the sensor cartridge;
    calculating either a particle number (PN) or particulate matter (PM) measurement for the emissions sample using data from the sensors; and
    directing the emissions sample out of the sensor cartridge through an emissions sample outlet defined by the sensor cartridge.

13. The method of claim 12, further comprising triangulating the data from the at least three sensors.

14. The method of claim 12, wherein the calculating uses a proportionality factor, a weighted linear integral factor, or a non-linear integral factor.

15. The method of claim 12, wherein each of the sensors is selected from the group consisting of a laser light opacity sensor, a light scattering sensor, a particle ionization sensor, a particle acoustic measurement sensor, and an electrostatic precipitation sensor.

16. The method of claim 12, further comprising:
    transmitting data from the sensors to a processing unit.

17. The method of claim 12, further comprising:
    receiving readings of an exhaust sample from the at least three different sensors, wherein each of the readings comprises at least one of a particulate matter and a particle number;
    applying a union function to the readings;
    applying an intersect function to the readings; and
    identifying a quantity of a pollutant within the exhaust sample.

18. The method of claim 17, wherein the quantity comprises a mass of particles, a number of particles, or a concentration of particles.

19. The method of claim 17, further comprising filtering the readings from the sensors prior to applying the union function or the intersect function.

20. The method of claim 17, wherein the identifying is based on at least one parameter associated with another exhaust sample.

21. The method of claim 17, further comprising triangulating the readings.

* * * * *